US011559807B2

(12) United States Patent
Tao et al.

(10) Patent No.: US 11,559,807 B2
(45) Date of Patent: Jan. 24, 2023

(54) SYSTEM AND METHOD FOR PRECISION DETECTION OF BIOMARKERS

(71) Applicant: Arizona Board of Regents on behalf of Arizona State University, Scottsdale, AZ (US)

(72) Inventors: Nongjian Tao, Fountain Hills, AZ (US); Wenwen Jing, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 277 days.

(21) Appl. No.: 16/689,530

(22) Filed: Nov. 20, 2019

(65) Prior Publication Data

US 2020/0156074 A1     May 21, 2020

Related U.S. Application Data

(60) Provisional application No. 62/770,056, filed on Nov. 20, 2018.

(51) Int. Cl.
| | |
|---|---|
| *G01N 33/543* | (2006.01) |
| *B01L 3/00* | (2006.01) |
| *G01N 1/38* | (2006.01) |

(52) U.S. Cl.
CPC ... *B01L 3/502761* (2013.01); *B01L 3/502715* (2013.01); *G01N 1/38* (2013.01); *G01N 33/54346* (2013.01); *G01N 33/54373* (2013.01); *B01L 2200/0647* (2013.01);
(Continued)

(58) Field of Classification Search
CPC ......... B01L 3/502761; B01L 3/502715; B01L 2200/0647; B01L 2300/06; B01L 2300/0627; B01L 2300/12; B01L 2300/168; B01L 3/00; B01L 3/50; G01N 33/54373; G01N 33/00; G01N 33/50
See application file for complete search history.

(56) References Cited

U.S. PATENT DOCUMENTS

| | | | |
|---|---|---|---|
| 2003/0096434 A1* | 5/2003 | Krutzik ............... | G01N 33/553 436/524 |
| 2003/0129665 A1* | 7/2003 | Sei ..................... | G01N 15/1475 435/7.2 |

(Continued)

OTHER PUBLICATIONS

Carcamo Yanez et al. "Development and Validation of an Ultrasensitive Procalcitonin Sandwich Immunoassay" High-throughput, vol. 6, No. 4, 2017, pp. 18.
(Continued)

*Primary Examiner* — Melanie Brown
*Assistant Examiner* — Jennifer H. Tieu
(74) *Attorney, Agent, or Firm* — Withrow & Terranova, P.L.L.C.; Vincent K. Gustafson

(57) ABSTRACT

A method for detecting biomarkers with shortened test time and maximized precision. A sample from the body fluid is made to flow over a sensor surface coated with a capture antibody to allow binding of a biomarker in the sample to the capture body. An optical method detects and counts the individual binding events along the sensor surface with single molecule resolution, and difference in the binding events along the sensor surface is detected in real time and analyzed to determine the biomarker concentration.

9 Claims, 35 Drawing Sheets

(52) U.S. Cl.
CPC ... *B01L 2300/06* (2013.01); *B01L 2300/0627* (2013.01); *B01L 2300/12* (2013.01); *B01L 2300/168* (2013.01)

(56) References Cited

U.S. PATENT DOCUMENTS

| | | | | |
|---|---|---|---|---|
| 2009/0117571 | A1* | 5/2009 | Solanki | G01N 33/5438 435/287.2 |
| 2011/0065597 | A1* | 3/2011 | Williams | G01N 33/557 506/9 |
| 2016/0003815 | A1* | 1/2016 | Nelson | B01L 3/5027 702/19 |
| 2016/0266105 | A1* | 9/2016 | Ismagilov | B01L 3/502715 |
| 2018/0292428 | A1* | 10/2018 | Murayama | G01N 35/1011 |

OTHER PUBLICATIONS

Chen et al. "Plasmon-Enhanced Colorimetric ELISA with Single Molecule Sensitivity" Nano Letters, vol. 11, No. 4, 2011, pp. 1826-1830.

Cheng et al. "Simultaneous Detection of Dual Prostate Specific Antigens Using Surface-Enhanced Raman Scattering-Based Immunoassay for Accurate Diagnosis of Prostate Cancer" ACS Nano, vol. 11, No. 5, 2017, pp. 4926-4933.

Cohen et al. "Single-Molecule Arrays for Protein and Nucleic Acid Analysis" Annual Review of Analytical Chemistry, vol. 10, No. 1, 2017, pp. 345-363.

Desmet et al. "Multiplex microarray ELISA versus classical ELISA, a comparison study of pollutant sensing for environmental analysis" Environmental Science Processes & Impacts, vol. 15, No. 10, 2013, pp. 1876-1882.

Diaconu et al. "Sepsis Biomarkers. Past, Present and Future" Farmacia, vol. 63, No. 6, 2015, pp. 811-815.

Fischer et al. "Emerging Technologies to Increase Ligand Binding Assay Sensitivity" The AAPS Journal, vol. 17, No. 1, 2015, pp. 93-101.

Gan et al. "Enzyme Immunoassay and Enzyme-Linked Immunosorbent Assay" Journal of Investigative Dermatology, vol. 133, No. 9, 2013, pp. e12.

Jarolim "High sensitivity cardiac troponin assays in the clinical laboratories" Clinical Chemistry and Laboratory Medicine, vol. 53, No. 5, 2015, pp. 635-652.

Liang et al. "Nanoplasmonic quantification of tumour-derived extracellular vesicles in plasma microsamples for diagnosis and treatment monitoring" Nature Biomedical Engineering, vol. 1, No. 4, 2017, pp. 1-11.

Liao et al. "A ultrasensitive ELISA method for detection of procalcitonin based on magnetic beads and enzyme-antibody labeled gold nanoparticles" Analytical Methods, vol. 8, 2016 pp. 1577-1585.

Liu et al. "Biomarkers for diagnosis of sepsis in patients with systemic inflammatory response syndrome: a systematic review and meta-analysis" SpringerPlus, vol. 5, No. 1, 2016, 10 pages.

Mordente et al. "Cancer Biomarkers Discovery and Validation: State of the Art, Problems and Future Perspectives" Advances in Experimental Medicine and Biology, vol. 867, 2015, pp. 9-26.

Nam et al. "Nanoparticle-Based Bio-Bar Codes for the Ultrasensitive Detection of Proteins" Science, vol. 301, No. 5641, 2003, pp. 1884-1886.

Pei et al. "Multiplexed Detection of Attomoles of Nucleic Acids Using Fluorescent Nanoparticle Counting Platform" Analytical Chemistry, vol. 90, No. 2, 2018, pp. 1376-1383.

Rhodes et al. "Surviving Sepsis Campaign: International Guidelines for Management of Sepsis and Septic Shock: 2016" Intensive Care Medicine, vol. 43, No. 3, 2017, pp. 304-377.

Rissin et al. "Single-molecule enzyme-linked immunosorbent assay detects serum proteins at subfemtomolar concentrations" Nature Biotechnology, vol. 28, No. 6, 2010, pp. 595-599.

Sajita et al. "Plasmonic-ELISA: expanding horizons" RSC Advances, vol. 6, No. 88, 2016, pp. 85440-85456.

Sevenler et al. Digital Microarrays: Single-Molecule Readout with Interferometric Detection of Plasmonic Nanorod Labels. Acs Nano 2018, 12 (6), 5880-5887.

Shrivastava "Methods for the determination of limit of detection and limit of quantitation of the analytical methods" Chronicles of Young Scientists, vol. 2, No. 1, 2011, pp. 21-25.

Solier et al. "Antibody-based proteomics and biomarker research— Current status and limitations" Proteomics, vol. 14, No. 6, 2014, pp. 774-783.

Sriram et al. "A rapid readout for many single plasmonic nanoparticles using dark-field microscopy and digital color analysis" Biosensors and Bioelectronics, vol. 117, 2018, pp. 530-536.

Thaxton et al. "Nanoparticle-based bio-barcode assay redefines "undetectable" PSA and biochemical recurrence after radical prostatectomy" PNAS, vol. 106, No. 44, 2009, pp. 18437-18442.

Tighe et al. "ELISA in the multiplex era: Potentials and pitfalls" Proteomics Clinical Analytics, vol. 9, 2015, pp. 406-422.

Twerenbold et al. "Clinical Use of High-Sensitivity Cardiac Troponin in Patients With Suspected Myocardial Infarction" Journal of the American College of Cardiology, vol. 70, No. 8, 2017, pp. 996-1012.

Twerenbold et al. "High-sensitive troponin T measurements: what do we gain and what are the challenges?" European Heart Journal, vol. 33, No. 5, 2012, pp. 579-586.

Uludag et al. "Cancer Biomarker Detection in Serum Samples Using Surface Plasmon Resonance and Quartz Crystal Microbalance Sensors with Nanoparticle Signal Amplification" Analytical Chemistry, vol. 84, No. 14, 2012, pp. 5898-5904.

Wang et al. "Label-free imaging, detection, and mass measurement of single viruses by surface plasmon resonance" PNAS, vol. 107, No. 37, 2010, pp. 16028-16032.

Yu et al. "Molecular Scale Origin of Surface Plasmon Resonance Biosensors" Analytical Chemistry, vol. 86, No. 18, 2014, pp. 8992-8997.

Yuan et al. "An ultrasensitive ELISA method for thedetection of procalcitonin based on magnetic beads and enzyme-antibody labeled gold nanoparticles" Analytical Methods, vol. 8, No. 7, 2016, pp. 1577-1585.

Zhao et al. "A photoacoustic immunoassay for biomarker detection" Biosensors and Bioelectronics, vol. 85, 2016, pp. 261-266.

Zhu et al. "Digital immunoassay of a prostate-specific antigen using gold nanorods and magnetic nanoparticles" RSC Advances, vol. 7, No. 44, 2017, pp. 27595-27602.

* cited by examiner

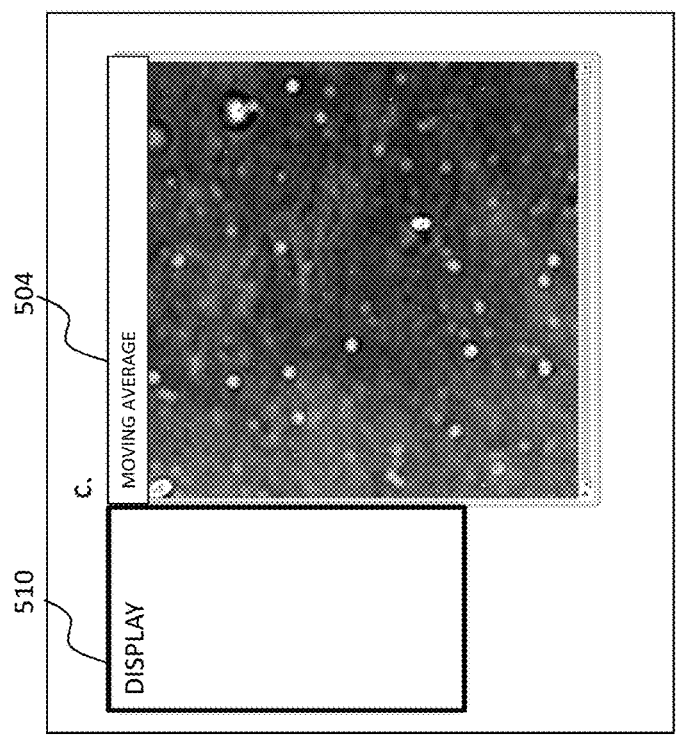
FIG. 5C
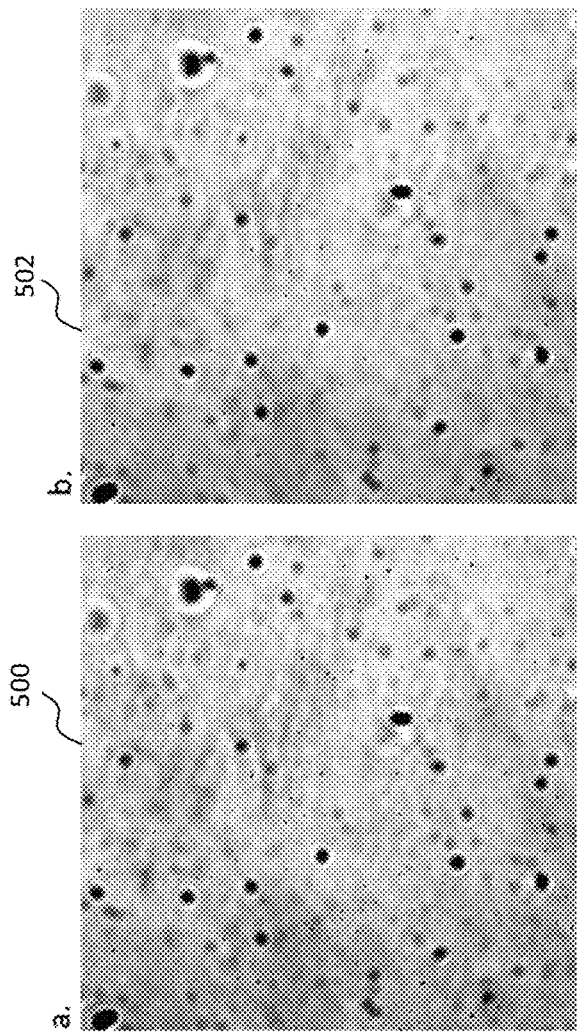
FIG. 5B
FIG. 5A

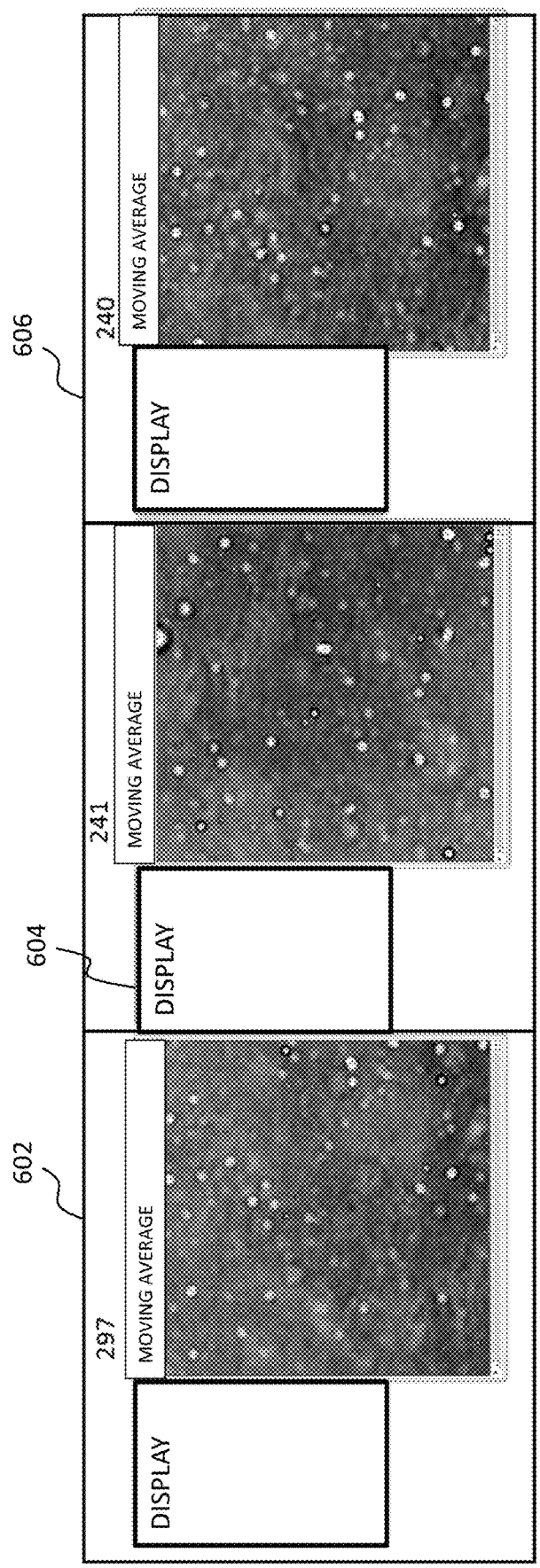

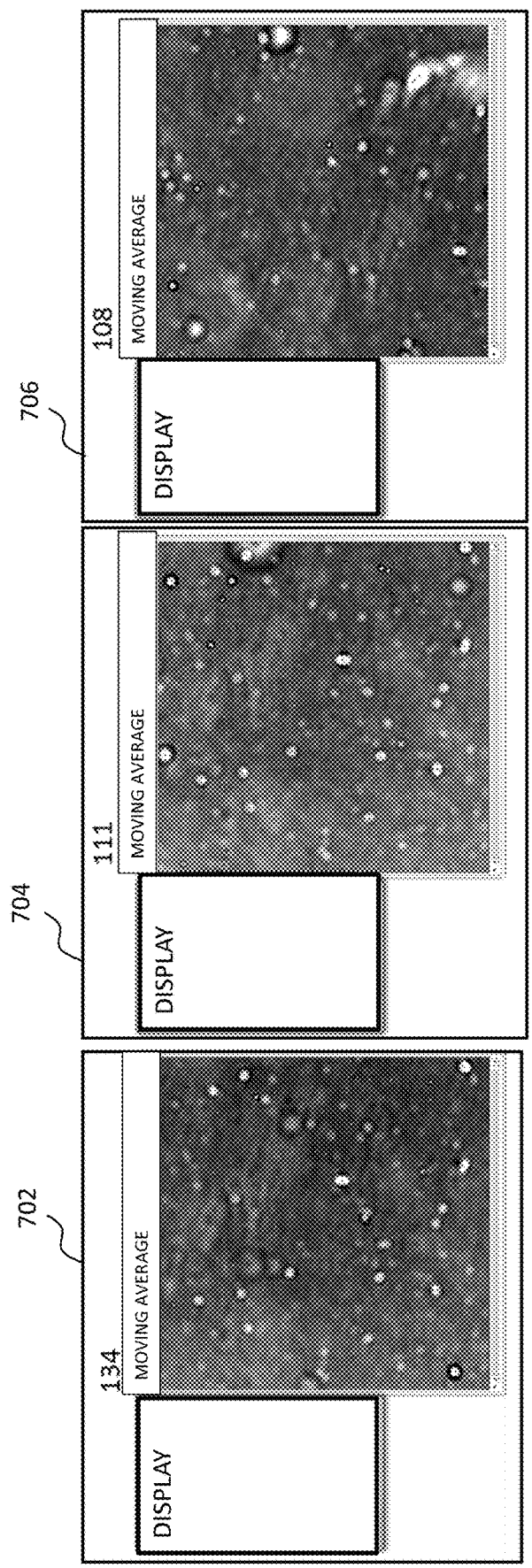

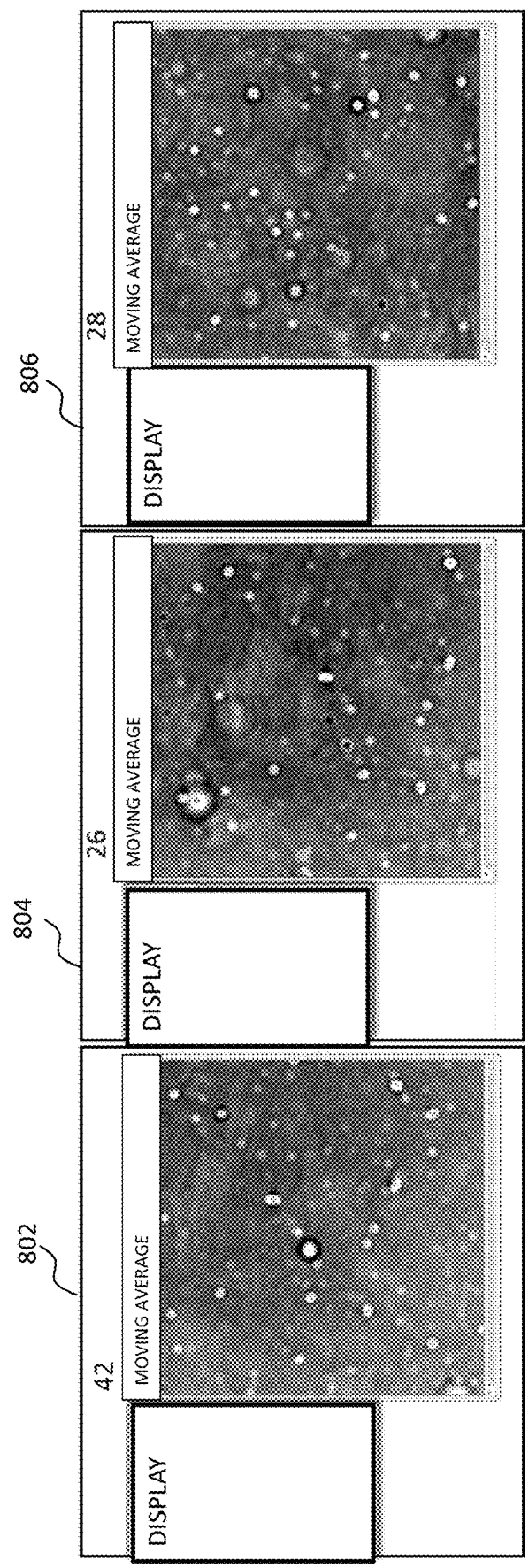

| Equation | $y = A2 + (A1 - A2)/(1 + (x/x0)^p)$ | | |
|---|---|---|---|
| Adj. R-Square | 0.99923 | | |
| | | Value | Standard Error |
| Mean | A1 | | 0.02554 |
| Mean | A2 | | 0.95428 |
| Mean | x0 | | 646.89814 |
| Mean | P | | 0.1127 |

FIG. 19

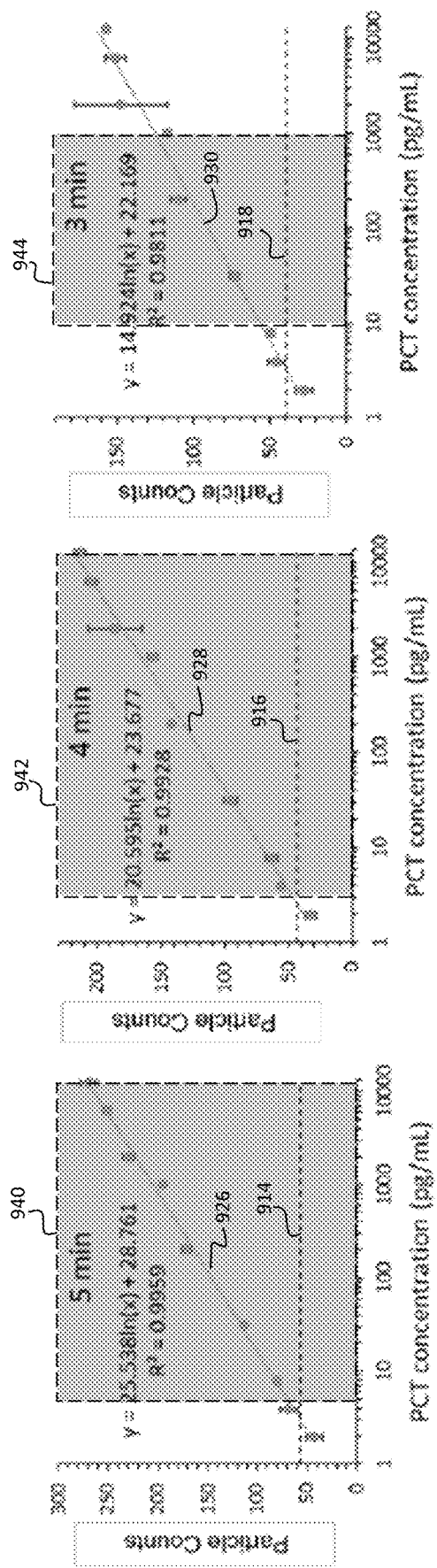

SYSTEM AND METHOD FOR PRECISION DETECTION OF BIOMARKERS

TECHNICAL FIELD

The method and system disclosed herein relates to rapid detection and precise quantification of molecular biomarkers in human blood and in other types of body fluids. The intended application of the method and system disclosed herein includes timely detection of acute diseases, including heart disease and sepsis, as well as monitoring of the disease progression.

BACKGROUND

Detection, identification and quantification of biomarkers, such as proteins, peptides, exosomes, hormones, neurotransmitters, metabolites and nucleic acids, are critical to disease diagnosis and progression monitoring[1,2]. Various approaches have been developed, but the most well-established strategy is to use antibodies. An antibody can recognize and bind to a biomarker (antigen) specifically, and the binding event is then converted into a readable optical, electronic, mechanical, or magnetic signal. A well-known device is lateral flow immunoassay using paper-based strips. These strips are based on visualization of human eyes, which are limited for non-quantitative applications, and insensitive for many clinical needs. To detect low concentration biomarkers, ELISA (enzyme-linked immunosorbent assay) has been developed, which amplifies antibody-biomarker binding via enzymatic reactions and converts reaction products into an optical signal (e.g., color changes). Although ELISA is the most established and powerful technique used in clinical and research labs, its limit of detection (LOD) and time required for testing are often insufficient for many clinical applications. The test time referred here in this disclosure is the time duration from the introduction of the sample into the system to reporting of the test results by the apparatus.

Recent technological advances have made it possible to detect single molecules, which have been used to measure the binding of a single biomarker molecule to a capture antibody with improved LOD and shorten test time. This single-molecule approach is referred to as digital immunoassay, one example is digital ELISA. To date, three platforms have been proposed to achieve digital immunoassay. They all rely on the antibody or antigen binding to a biomarker molecule but differ in the platform used to detect the biomarker-antibody or antigen binding events.

The first platform is to replace the large reaction well in the traditional ELISA with an array of microwells[3,4]. The volume of the microwells is small, such that each microwell has either no biomarker present or a single biomarker molecule that binds to capture antibody conjugated with a magnetic bead in the microwell. In the former case, no enzymatic reaction takes place, and fluorescence readout from the microwell is null (or background level). In the latter case, however, the enzymatic reaction products lead to fluorescence emission, which is detected as a binding event.

The second digital immunoassay platform combines single molecule fluorescent detection with flow cytometry[5]. A sample solution containing a biomarker is incubated with a capture antibody attached either to a plate or a bead. This will allow the binding of the biomarker to the capture antibody. After the incubation, a buffer solution is introduced to wash away unbound biomarkers. A second (detection) antibody conjugated to an alexa fluor tag is then added to the sample for further incubation, followed by second washing. A neutralization buffer is added to break the detection antibody-biomarker complex from plate or bead, which flows through a narrow capillary crossing a laser beam to emit a fluorescent signal detected with a photodetector.

The third platform uses metal nanoparticles (e.g., gold) as a signal readout mechanism[6-8]. The nanoparticles bind to the biomarkers captured on a sensor surface and detected individually via dark field, interference and plasmonic optical imaging techniques. Using gold nanorods (GNRs) it has been shown that the polarization of the GNRs provides additional information that help detection of molecular binding.[6]

These digital immunoassay technologies provide single molecule detection capability, which significantly improves the LOD of the traditional ELISA. However, the improvement is often achieved at the expense of test time. Another more important remaining drawback of these digital immunoassay technologies is the lack pf precision. Fast and precise detection are crucial for disease diagnosis and treatment[9].

An important example is cardiovascular diseases, where timely and precise assessment of the patient condition is often a matter of life or death[9,10]. A well-established biomarker in cardiovascular disease is troponin(s), which is a complex of three regulatory proteins including troponin C (TnC), troponin I (TnI) and troponin T (TnT). The troponin complex (e.g., Troponin T) concentration in human blood varies over an extremely broad range, from as low as a few ng/L in healthy population to as high as $10^4$ ng/L[11] in patients with cardiovascular disease. This requires a detection technology not only with sufficient low LOD but also with wide dynamic range. In the case of cardiovascular diseases, monitoring troponin level of a patient with a time interval of 10-20 mins or shorter is highly desired for the doctor to diagnose the condition, assess the disease progression and evaluate the outcome of medication. This requires a fast and precise detection technology. High precision is needed because the change in the troponin level of the patient can be rather small, and thus difficult to resolve with conventional detection technologies[11]. The current technologies fall into two categories. One category is precise but slow. The other one is fast but imprecise. There is a need of both fast and precise detection technology for timely assessment of biomarker level, such as troponin. The detection technology must also have low LOD and wide dynamic range because of the wide distribution of biomarker levels for different people.

The method and system disclosed herein aims to address this unmet need.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to use as an aid in determining the scope of the claimed subject matter.

A system for quantitative detection of biomarkers in a fluid includes a fluidic microchannel including a surface partitioned into a plurality of zones. An illumination source is positioned to illuminate the microchannel with light that is transmitted through the plurality of zones. A delivery device is positioned for introducing a fluidic sample containing one or more biomarkers to the microchannel. A sensor, coupled to the microchannel, having a surface for generating sensor signals for individual binding events, the surface including at least two zones coated with a first antibody, wherein the fluidic sample flows to a first zone and then a second zone to allow the biomarkers to bind onto the sensor surface in the first zone where a portion of biomarkers not bound in the first zone are bound to the sensor surface or antibodies in the second zone. The microchannel may be of any useful geometric shape that allows flow such as straight, curved or zig-zagged to maximize the channel length.

A detector located in the system produces an optical readout representing the individual binding events of each of the individual biomarkers to the sensor surfaces of the first zone and the second zone in real time. An image system including a data processing unit is coupled to receive the optical signals and quantify the individual binding events on the sensor surfaces of the first zone and the second zone and determines the difference in the numbers of binding events on the first and second zones.

A key enabling component of the present invention is the introduction of detecting of the difference in the number of binding events on two or more zones along the fluidic channel. This difference can also be expressed as a gradient in the number of binding events along the microchannel. This is in contrast to prior arts, which detect an absolute binding number on the sensor surface. The difference or gradient approach removes non-specific binding associated with various species in a practical sample that interfere with the detection of a particular disease biomarker. Another key component is real time digital counting of the individual binding events, which improves the accuracy and precision. It also allows optimizing the detection time for a particular application. This is because the precision usually increases with detection time, so there is a compromise between the two. Prior arts teach the detection over a predefined time interval. In the present invention, the detection takes place in real time, so that one can adjust the detection time based on the detection results and need of a particular application. In other words, for a highly concentrated biomarker sample, binding of the biomarker takes place quickly, which produces statistically significant readings and thus allows precise detection with a short detection time. On the other hand, for a dilute biomarker sample, the apparatus of the present invention can be adapted to detect the sample over a longer time until satisfactory precision is achieved. An additional enabling component is the simple optical imaging based on light scattering and surface plasmon resonance. Traditional light scattering imaging is noisy for detecting nanoparticles. The present innovation teaches methods to minimize noise and allows imaging of single nanoparticles (each corresponds to a binding event of the biomarker molecule to an antibody).

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings and figures.

FIG. 5A-5C show progressively processed enlarged microscopic images of image processing.

FIG. 6A-FIG. 6C show computer screenshots of 3 different regions of zone 1 as recorded by the image system and analyzed by ImageJ software.

FIG. 7A-FIG. 7C show computer screenshots of 3 different regions of zone 2 as recorded by the image system and analyzed by ImageJ software.

FIG. 8A-FIG. 8C show computer screenshots of 3 different regions of zone 3 as recorded by the image system and analyzed by ImageJ software.

FIG. 19 is a table of values corresponding to the plot of FIG. 18.

FIG. 20A-FIG. 20F show standard curves of PCT detection at different time points.

Figure 1:
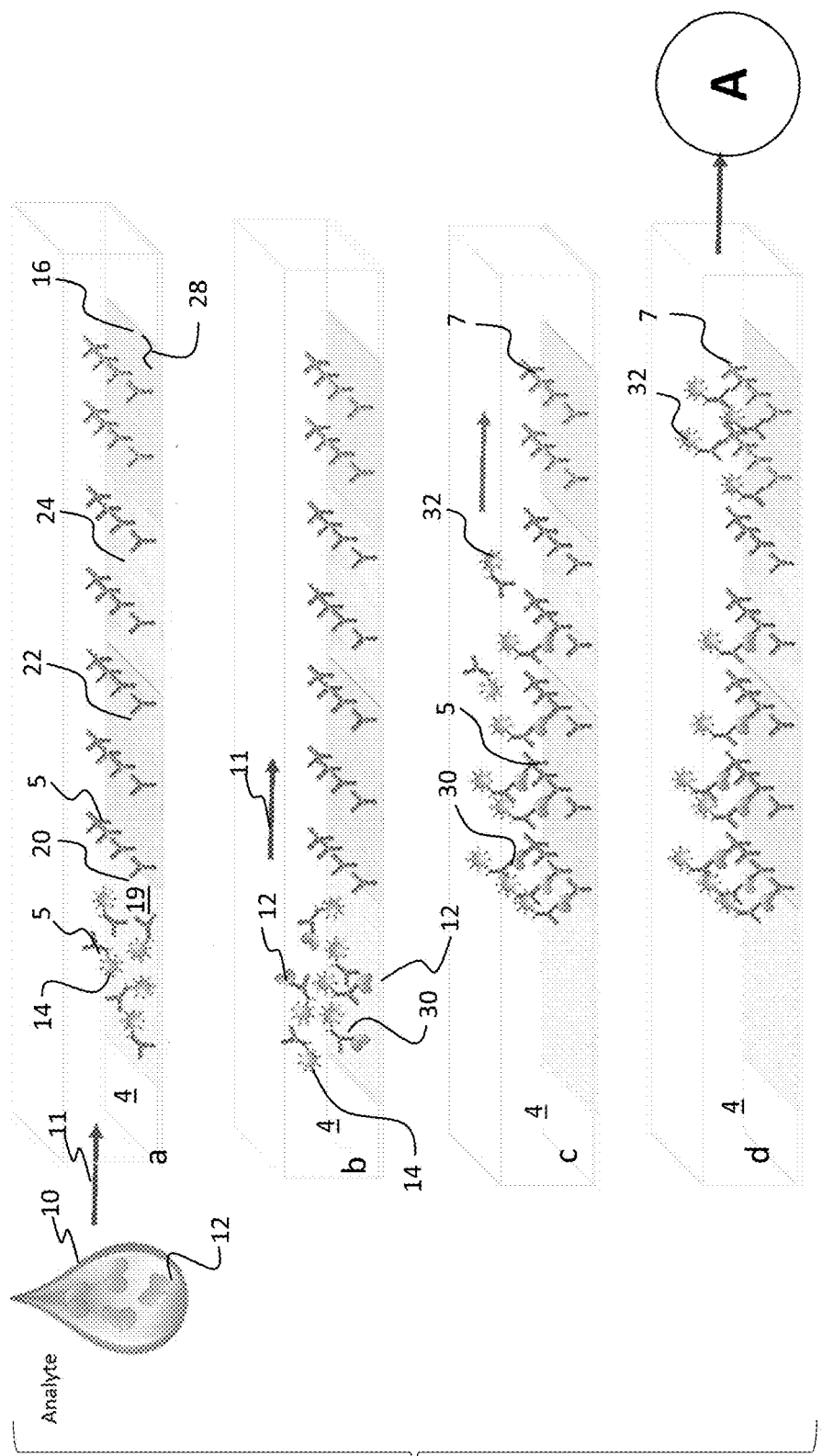
FIG. 1 schematically shows an overview of the detection principle in a time sequence a-d as employed in one example of the biomarker detection apparatus.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements and have been solely selected for ease of recognition in the drawings.

DETAILED DESCRIPTION

The following disclosure describes a system and method for detection, identification and quantification of biomarkers in human samples. Several features of methods and systems in accordance with example embodiments are set forth and described in the figures. It will be appreciated that methods and systems in accordance with other example embodiments can include additional procedures or features different than those shown in the figures. Example embodiments are described herein with respect to systems and methods for a large view and low noise optical imaging system. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of microarray technology:

The articles "a" or "an" and the phrase "at least one" as used herein refers to one or more.

As used herein, "enzyme-linked immunosorbent assay (ELISA)", is an assay technique designed for detecting and quantifying substances such as peptides, proteins, antibodies, hormones other biological species, such as carbohydrates.

As used herein, "filtering" or "applying a filter" has its normally accepted meaning as digitally filtering a signal, such as an image either in the spatial or frequency domain. For example, filtering includes a neighborhood operation, in which the value of any given pixel in the output image is determined by applying some algorithm to the values of the pixels in the neighborhood of the corresponding input pixel. A pixel's neighborhood is some set of pixels, defined by their locations relative to that pixel. Linear filtering is filtering in which the value of an output pixel is a linear combination of the values of the pixels in the input pixel's neighborhood.

As used herein, "plurality" is understood to mean more than one. For example, a plurality refers to at least two, three, four, five, ten, 25, 50, 75, 100, 1,000, 10,000 or more.

"Obtaining" is understood herein as manufacturing, purchasing, or otherwise coming into possession of.

As used herein, "real time" means responding to input immediately or within a time period between event and response that is imperceptible to a user.

As used herein, "Surface Plasmon Resonance (SPR)" is a phenomenon that occurs when polarized light hits a metal film at the interface of media with different refractive indices.

Referring now to FIG. 1, an overview of the detection principle is schematically shown in a time sequence a-d. At an initial time a, a body fluid 10 containing an analyte 12 such as, for example, a target biomarker, is introduced to a fluidic channel 4 and flows over a sensor surface 16 in an entry zone 19 that may optionally be coated with detection conjugated tag antibodies 20. It is important to note that the process may also be carried out without conjugation as expanded upon below. The sensor surface 16 may be partitioned into the entry zone 19, a first zone 22 (zone 1), a second zone 24 (zone 2) and a third zone 28 (zone 3). The body fluid 10 is introduced to the fluidic channel 4 by a known delivery device (not shown). The direction of flow is in the direction represented by the directional arrows 11.

Note that the entry zone, zone 1, zone 2 and zone 3 are located along the channel between the entrance and exit of the channel. They are not necessarily physically defined regions in the channel, but are selected as regions at selected locations along the channel by a computer software algorithm. In order to compare a first zone to a second zone, a pair of zones are selected by a computer software algorithm. The zones are not necessarily sequential or located adjacent to one another.

Figure 10:
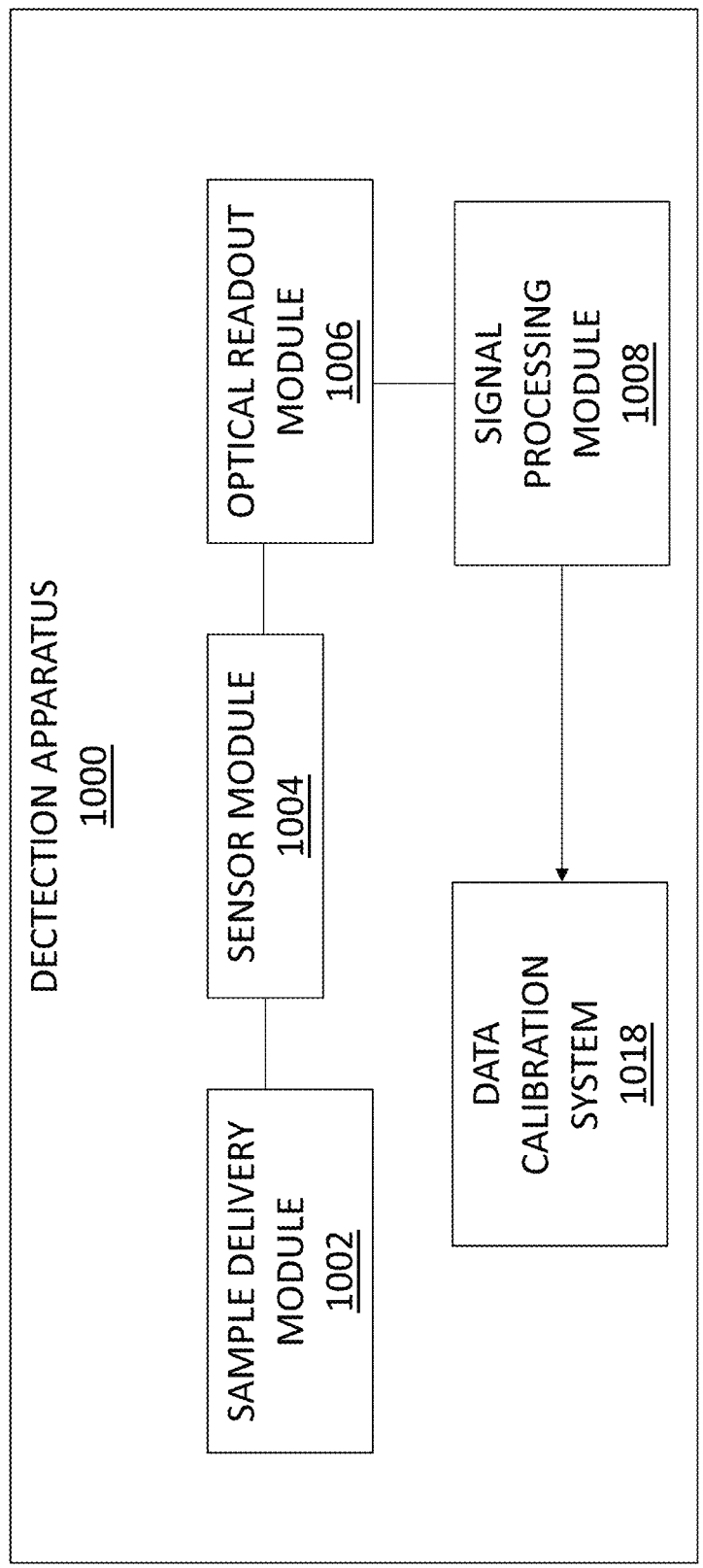
FIG. 10 schematically shows an example of a biomarker detection apparatus.

The analytes 12 form an antibody-analyte complex 30 with the conjugated tag antibodies 14. At time sequence b, detection of the antibody-analyte complex is made by a sensor chip (as shown in FIG. 10). Then, at time sequence c, the antibody-analyte complex flows into the first zone 22 where the sensor surface is coated with a capture antibody 5. Binding of the biomarker tag 14 to the antibody is detected with single molecule precision to allow counting of the individual binding event in real time with an optical imaging system. Finally, at time sequence d, remaining detection antibody 32 that is not bound to the analyte then flows into the third zone 28 and binds to the anti-detection antibody to ensure a reliable test. In some useful examples the method and system disclosed herein can be used for detection, identification and quantification of biomarkers, such as proteins, peptides, exosomes, hormones, neurotransmitters, metabolites and nucleic acids.

Figure 2:
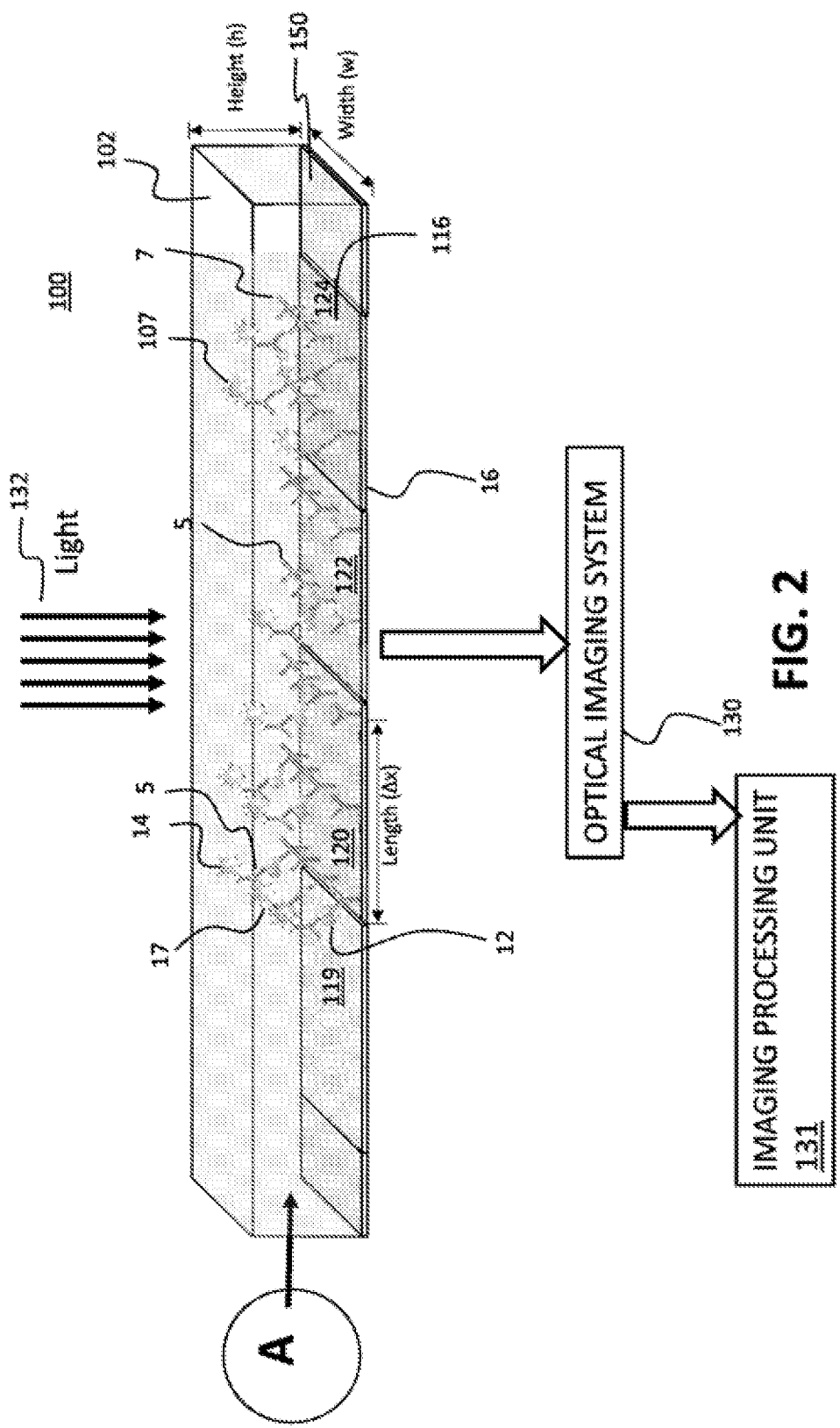
FIG. 2 schematically illustrates a diagram of an example of a biomarker detection apparatus.

Referring now to FIG. 2, a schematic diagram of an example of a biomarker detection system is shown. A biomarker detection system 100 includes a fluidic microchannel 102 containing different regions on a surface 16. In the system as shown, antibodies 5, 7 have previously been coated onto the surface. As described above with respect to the principles, an entry zone 119 may optionally be coated with the detection conjugated tag antibody. A first zone and a second zone 120, 122 respectively may be coated with capture antibodies 5 for testing and self-referencing. A third zone 124 is coated with anti-detection antibody 7 for quality reference. The dimensions of the microfluidic channel are denoted by w and h representing the width and height of the fluidic channel, and $\Delta x$ represents the length of zone 1 along the fluidic channel.

In operation, a body fluid containing an analyte 12 is introduced to the fluidic microchannel 102 and flows over the surface 116. In one example, the surface 116 may optionally be coated with a plurality of detection conjugated tag antibodies in order to enhance the detection signal. in this case, a plurality of detection antibody-analyte complexes 17 are formed. Then the plurality of detection antibody-analyte complexes 17 flow to a downstream portion of the sensor surface, namely first zone 120, coated with a capture antibody 5. Light 132 illuminates the microchannel 102 and the analytes within and resultant optical signals are transmitted to the detector 150. Binding of the conjugated tag antibody biomarkers to each antibody-analyte complex 17 is detected with single molecule precision to allow counting of the individual binding event in real time with an optical imaging system 130 which is located to receive signals from the sensor in real time. The optical imaging systems is coupled to transmit data to an image processing unit 131. The remaining detection conjugated tag antibodies 107 that are not bound to the analyte then flow into the third zone 124 and bind to the anti-detection antibody 7 to be counted by the image system as, for example, an internal reference to ensure a reliable test.

As will be understood with reference to FIG. 1 and FIG. 2, in one example detection of the biomarkers may be accomplished by detecting antibodies bound to a biomarker molecule. In another more complex example, quantitative detection of a biomarker may be accomplished by introducing a fluidic sample containing the biomarker and particles coated with a second antibody to the sensor surface along the microchannel to allow the binding of the biomarker to the first and second antibody. In yet another even more complex example, quantitative detection of a biomarker may be accomplished by allowing the binding of the biomarker to the first antibody, and then introducing a fluidic sample containing particles coated with a second antibody and allowing binding the particles to biomarkers that bind to the first antibody on the sensor surface.

To expand upon the above, in one example a system for quantitative detection of a biomarker in a fluid, includes a fluidic microchannel; a sensor surface on which an antibody that can bind specifically with the biomarker; a delivery device for introducing a fluidic sample containing the biomarker to the sensor surface along the microchannel and allow the binding of the biomarker to the antibody; an illumination source positioned to illuminate the sensor surface; an optical imaging system that captures light scattered by the individual binding events of the biomarker molecule to the antibody on the sensor surface; an image processing unit to quantify the individual binding events on the sensor surface at least two zones along the flow direction, and determines the difference in the numbers of binding events on the first and second zones, and a data calibration system that correlates the difference in the number of binding events on the first and second zones to the concentration of the biomarker.

In yet another example, in a system for quantitative detection of a biomarker in a fluid, includes a fluidic microchannel; a sensor surface on which a first antibody attached; a delivery device for introducing a fluidic sample containing the biomarker and particles coated with a second antibody to the sensor surface along the microchannel and allow the binding of the biomarker to the first and second antibody; an illumination source positioned to illuminate the sensor surface; an optical imaging system that captures light scattered by the particles; an image processing unit to count the particles in real time, and determines the difference in the numbers of particles on the first and second zones, and a data calibration system that correlates the difference in the number of particles on the first and second zones to the concentration of the biomarker.

In yet another example, a system for quantitative detection of a biomarker in a fluid, includes a fluidic microchannel; a sensor surface on which a first antibody is attached; a delivery device for sequentially introducing a fluidic sample containing the biomarker to the sensor surface along the microchannel and allow the binding of the biomarker to the first antibody, and then a fluidic sample containing particles coated with a second antibody and allow binding the particles to biomarkers that bound to the first antibody on the sensor surface; an illumination source positioned to illuminate the sensor surface; an optical imaging system that captures light scattered by the particles; an image processing unit to count the particles in real time, and determines the difference in the numbers of particles on the first and second zones, and a data calibration system that correlates the difference in the number of particles on the first and second zones to the concentration of the biomarker.

Figure 3:
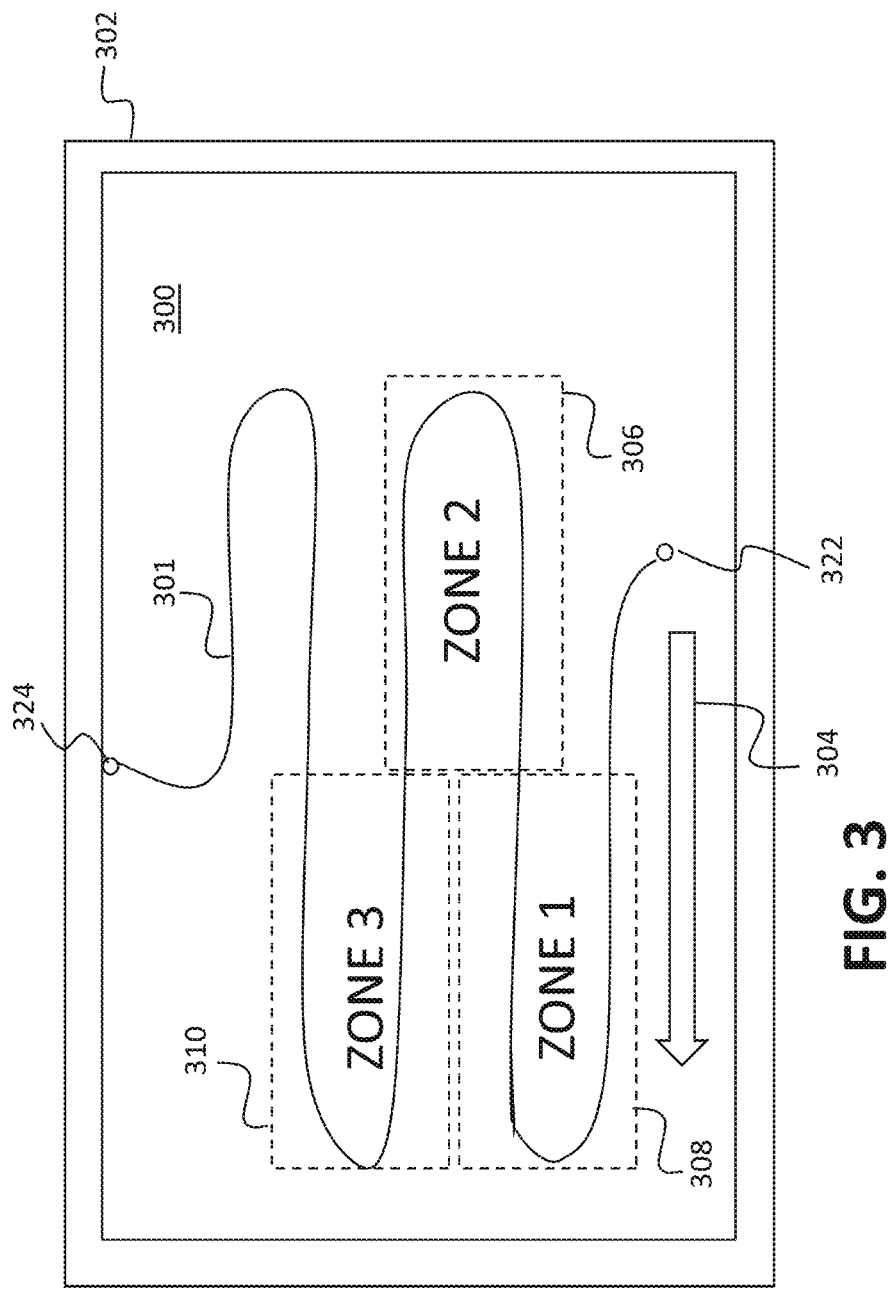
FIG. 3 schematically shows an illustration of an example of a microfluidic chip as employed in the disclosed apparatus.

Referring now to FIG. 3, an illustration of an example of a microfluidic chip as employed in the disclosed system is schematically shown. A microfluidic chip 300 includes a microfluidic channel 301 that is bonded to a detection chip 302. As described above, the microfluidic channel 301 includes at least 3 partition zones, as selected by a computer algorithm, indicated as zone 1, zone 2 and zone 3 as designated by broken line boxes 308, 306 and 310 respectively. In operation, analyte is introduced at an input port 322 and flows through the microfluidic channel 2 through zones 1, 2 and 3 to outlet port 324 in the direction indicated by directional arrow 304. As the analyte flows through the microfluidic channel it is held at each zone for a predetermined time reaction then move to the next zone. The binding signal is collected by the detector which sends detected binding signals to an image system which includes a processor for running the software analysis on the detected signals.

Figure 4:
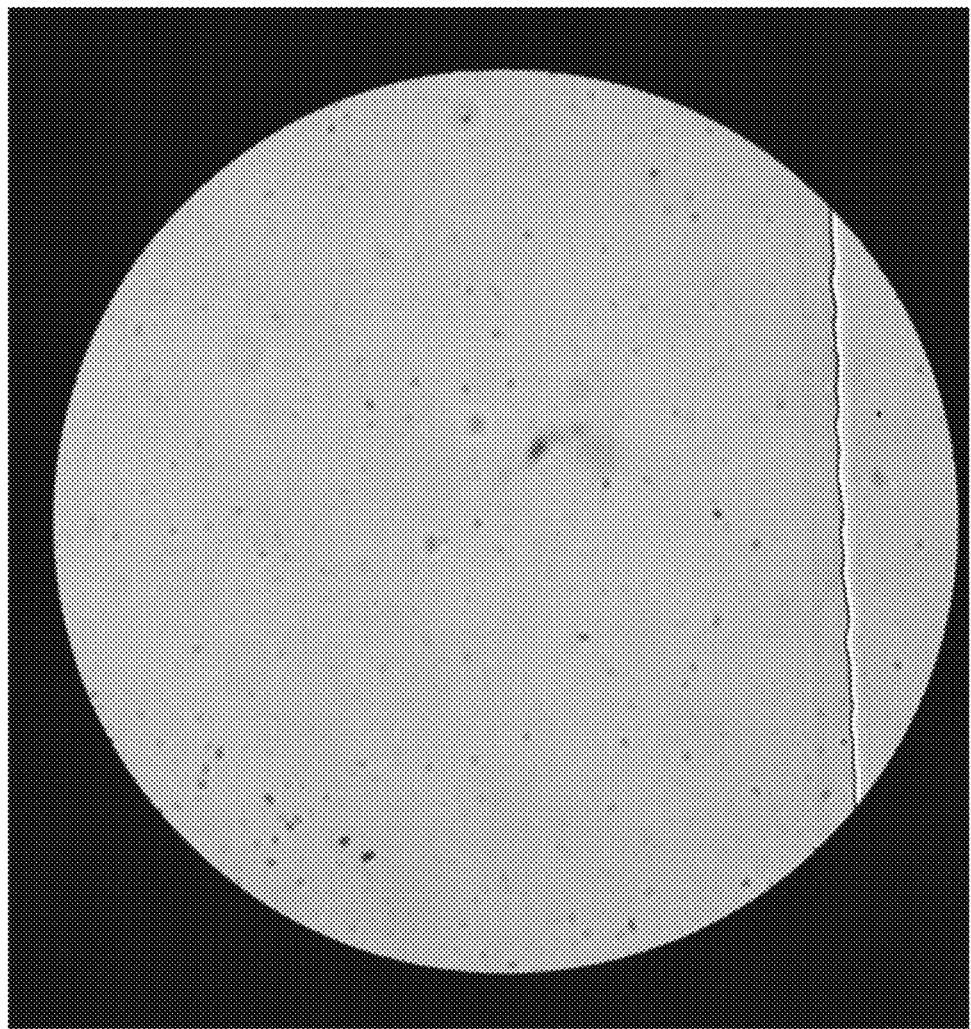
FIG. 4 shows an enlarged microscopic image of an example of binding events.

Referring now to FIG. 4, an enlarged microscopic image of an example of binding events is shown. In one example binding events were recorded by an image system in real time in a magnification of 20× (via 40× high numerical aperture objective, zoom out 0.5×). The frame rate is 20 fps.

Referring now to FIG. 5A-5C, progressively processed enlarged microscopic images of image processing are shown. The image processing for one example comprises three major steps. Referring specifically to FIG. 5A, A 700×700 pixel image sequence 500 is first loaded into imaging software in the image system, as for example commercially available ImageJ software. Referring specifically to FIG. 5B, the resulting image 502 of a moving average command applied to remove any background pattern and reduce any shot noise shown. Finally, referring specifically to FIG. 5C, a screenshot an image 504 after a software tracking command is used to count the binding signal in realtime is shown. A display 510 generated by the imaging software is also shown.

Referring now to FIG. 6A-FIG. 6C, computer screenshots of 3 different regions of zone 1 as recorded by the image system and analyzed by ImageJ software are shown. The count number of these region of zone 1 are as shown, namely 297, 241 and 240 respectively in screenshots 602, 604 and 606 respectively. When the analyte solution flows through and stays in zone 1, the analyte concentration is high, thus the antibodies can capture more analytes than zone 2 and zone 3 at the same time.

Referring now to FIG. 7A-FIG. 7C, computer screenshots of 3 different regions of zone 2 as recorded by the image system and analyzed by ImageJ software are shown. The count number of these region of zone 2 are as shown, namely 134, 111 and 108 respectively in screenshots 702, 704 and 706 respectively. After the analyte solution has flowed through and remains in zone 1, the remaining uncaptured analyte then flows into zone 2 and binds to the capture antibody in zone 2. Due to analyte consumption in zone 1, the analyte concentration in zone 2 is lower than the concentration at which it flows through zone 1.

Referring now to FIG. 8A-FIG. 8C, computer screenshots of 3 different regions of zone 3 as recorded by the image system and analyzed by ImageJ software are shown. The count number of these region of zone 3 are as shown, namely 42, 26 and 28 respectively in screenshots 802, 804 and 806 respectively. After the analyte solution has flowed through and captured analyte remains in zone 1 and zone 2, the remaining uncaptured analyte then flows into zone 3 and binds to the capture antibody in zone 3. The analyte concentration in zone 3 is lower than the concentration at which it flows through Zone 1 and zone 2. The trend of this concentration gradient in zone 1, 2, and 3 can be used as a self-reference as well as a calculation to evaluate non-specific adsorption.

Figure 9:
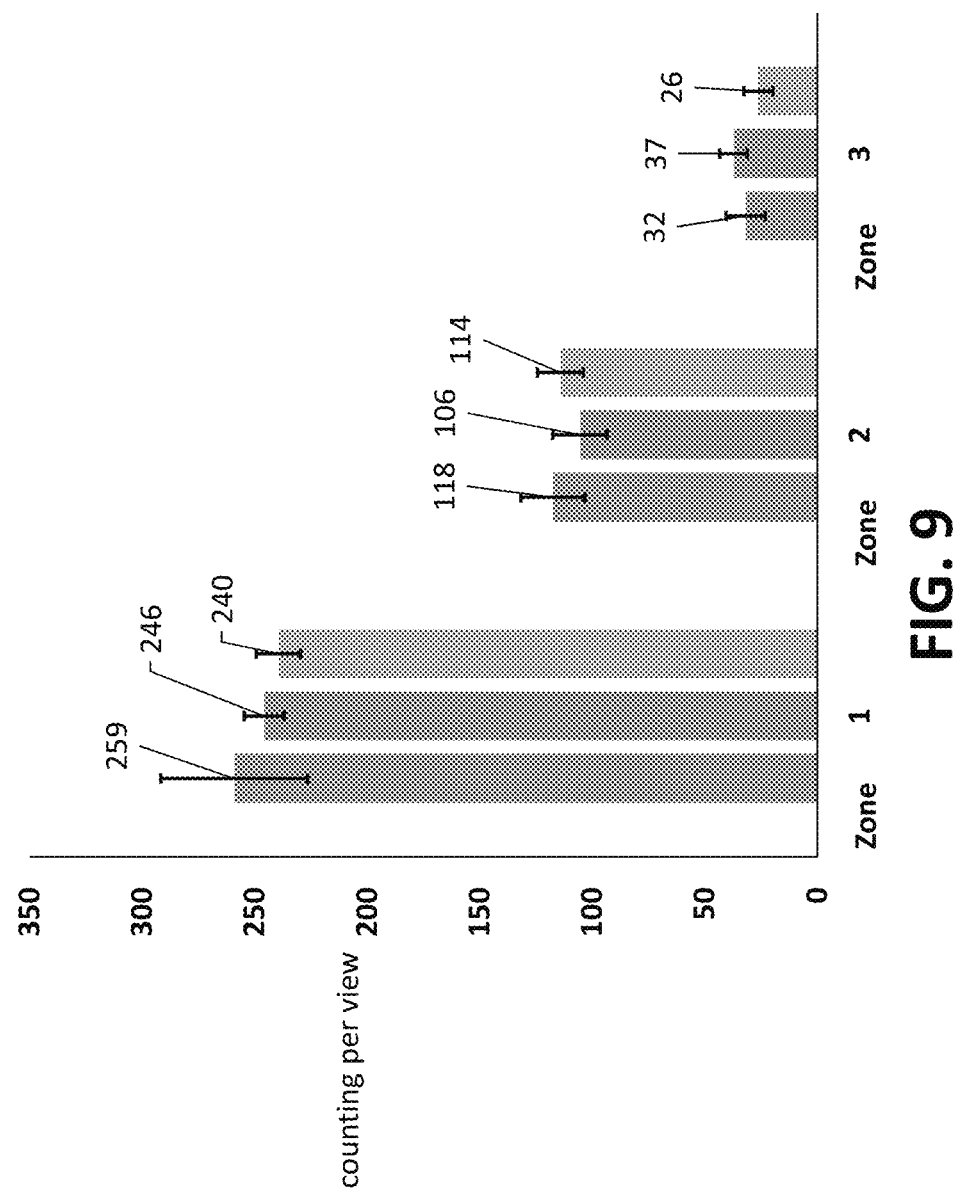
FIG. 9 shows a histogram is shown for an example using beads.

Referring now to FIG. 9, a histogram is shown for an example using beads. The histogram shows the bead count result in different parts of the channel (zone 1, 2, and 3). For each zone, perform a triple parallel test (shown in the figure as blue, orange, and gray, respectively). For each test, three different regions of each zone were used to calculate the average count. The number of beads counting per view reflects the binding signal, the large number corresponds to a strong signal. Error bars are the standard deviation over triplicate regions of each view. The concentration of PCT solution is 20 pg/mL. The results show that there were significant differences in the beads count results in different parts. The signal gradually weakens in the direction of flow, the signal near the inlet is large, and the signal near the outlet is weak.

Referring now to FIG. 10, there schematically shown is an example of a biomarker detection apparatus. A biomarker detection system 1000 may include a sample delivery module 1002, a sensor module 1004, an optical readout module 1006, a signal processing module 1008 and a data calibration system 1018.

Sample Delivery Module

The sample deliver module 1002 introduces a blood or other human sample to the apparatus. It may also contain a means to remove non-biomarker components (blood cells, platelets etc.) via filters, centrifuge or gravimetric mechanisms, before delivering the sample to the apparatus.

Sensor Module

The sensor module 1004 features a fluidic channel (as best shown in FIG. 3) to guide the sample to flow over a sensor surface on which a capture antibody is immobilized to bind to the biomarker. As described above, the sensor surface is connected to a detector that registers binding events and transmits optical or optical electrical signals to the image system representing the binding events. When an analyte is introduced into the system, the sensor surface of the upper stream has more binding events than that of the downstream surface because of the depletion of the biomarker in the fluid associated with the binding. This creates a decreasing number density of the biomarker bound along the sensor surface in the direction of the flow. In other words, the sensor surface in the upper stream has more binding than that in the downstream surface. This decreasing number density can be described as a gradient or a difference in the binding at two locations (zone 1 and zone 2), where the fluidic sample flows over zone 1 first and then over zone 2.

The biomarker level in the body fluid is more precisely determined from the difference signal from the two zones than detection at a single location or averaging over the entire sensor surface. The principle of this difference detection (internal reference) is summarized below:

The counts at zone 1 and zone 2 are denoted as $N_1$ and $N_2$, respectively, each including specific binding of the biomarker ($N_{spec}$) and non-specific ($N_{non-spec}$) binding of the second antibody-conjugated nanoparticles, as well as common noise. Common noise here is referred to as any noise appear in both zone 1 and zone 2. Examples of common noise are light source instability, temperature and mechanical drifts. This results in the following relationships, $$N_1 = N_{spec,1} + N_{non\text{-}spec,1} + \text{common noise} \tag{1}$$

$$N_2 = N_{spec,2} + N_{non\text{-}spec,2} + \text{common noise} \tag{2}.$$

If assuming that the non-specific adsorption is uniform along the channel, then $N_{non\text{-}spec,1} = N_{non\text{-}spec,2}$, and $$N_1 - N_2 = N_{spec,1} - N_{spec,2}, \tag{3}$$

which removes non-specific adsorption and common noise in the system. In other words, the detection at zone 2 serves as an internal reference to remove non-specific adsorption and common noise. Note: Two zones described here serve the purpose of illustrating the invention. Analysis of binding events at multiple locations (multiple zones) or even every position along the channel continuously can also be used.

Referring again to FIG. 1, one example of the internal reference, where sample solution flows along a fluidic channel from left (entrance) to right (exit) over a sensor surface coated with a capture antibody as illustrated. Two zones are defined on the sensor surface, zone 1 and zone 2, along the flow from the upper surface to the downstream surface. The biomarker concentration from the sample as denoted as $c_0$, binding affinity of the biomarker to the capture antibody as $K_D$, number density of the capture antibody as b, biomarker concentration in zone 1 (upper stream) as $c_1$, biomarker concentration in zone 2 (lower stream) as $c_2$. For the sake of explaining the principle of the method and system disclosed herein, the sample fluid is introduced to zone 1 to allow incubation over sufficient time so that the binding and unbinding of the biomarker to the capture antibody reach thermal equilibrium. It is further assumed that $K_D$ is much greater than $c_0$. Without these assumptions, details may change but the basic conclusions remain the same. With these two assumptions, the number density of biomarker molecules bound on the capture antibody is simply expressed as $$n_1 = \frac{c1}{K_D}b. \quad (1)$$

Binding of biomarker to capture antibody in zone 1 leads to deplete of biomarker in the fluid by an amount of $$\frac{c1}{K_D}b(w\Delta x), \quad (2)$$

where w and h are the width and height of the fluidic channel, and $\Delta x$ is the length of zone 1 along the fluidic channel. Consequently, the biomarker concentration in the fluid in zone 1 will drop to c1, which is determined by the following equation, $$\frac{c1}{K_D}b(w\Delta x) + c1w\Delta xh = c0w\Delta xh. \quad (3)$$

Solving equation 3 leads to $$c1 = \frac{K_D h}{K_D h + b}c0. \quad (4)$$

$N_1$, the number of biomarker molecules bound to the capture antibody in zone 1 observed by the optical imaging system, is $$N_1 = c_1\left(\frac{b}{K_D}\right)A = c0\left(\frac{K_D h}{K_D h + b}\right)\frac{b}{K_D}A, \quad (5)$$

where A is the area of imaging view.

Similarly, $N_2$, the number of biomarker molecules bound to the capture antibody in zone 2 observed by the optical imaging system, is given by $$N_2 = c_2\left(\frac{b}{K_D}\right)A = c0\left(\frac{K_D h}{K_D h + b}\right)^2\frac{b}{K_D}A. \quad (6)$$

The difference signal, $N_1-N_2$, is $$N_1 - N_2 = c0\left(\frac{K_D h}{K_D h + b}\right)\left(1 - \frac{K_D h}{K_D h + b}\right)\frac{b}{K_D}A. \quad (7)$$

Eq. 7 shows that the difference signal is indeed proportional to the biomarker concentration (c0) in the sample. It also shows that the maximum difference occurs when $K_D h \ll b$, which means that lower channel height (h) is and higher capture antibody concentration will be. typically use a few tens of microns for The channel height may typically be a few tens of microns, but it can extend up to about 1 mm.

The analysis above assumes the length of zone 1 is the same as that of zone 2. One can also use a large length for zone 1 to maximize binding (thus depletion in zone 1) and the difference signal. An alternative approach is to include an additional zone between zone 1 and zone 2. Additionally, one can maximize biomarker binding capacity by increasing the surface area of this additional zone.

The embodiment described above flows a sample fluid to zone 1 and allows for an incubation period before flowing to the next zone. An improved embodiment is to flow a fluidic sample along the channel continuously without stopping. The mathematical derivation of the detection signal ($N_1-N_2$) will not be the same (more complex), but the basic principle remains unchanged.

Optical Readout Module

The optical readout module 1006 features a wide view and low noise imaging for real time detecting of the binding of a second antibody preferably conjugated on nanoparticles to the biomarker bound on the capture antibody. Two key innovative features stand out of this disclosure are wide-view detection and real time single nanoparticle counting as explained below.

The wide view imaging of single biomarker molecule detection enables low LOD. Digital immunoassay can detect the binding of a single biomarker. However, LOD is how low a biomarker concentration in the body fluid one can precisely determine over a given period of time. This is determined by the binding affinity ($K_D$) of the biomarker to the capture antibody, surface density of the capture antibody (b), and area of the sensor surface that can be imaged (A), according to Eq. 5 and Eq. 6. The relative standard error is $$\left[c_0\left(\frac{K_D h}{K_D h + b}\right)\frac{b}{K_D}A\right]^{-1/2}. \quad (8)$$

For a given biomarker concentration ($c_0$) and binding affinity ($K_D$), the larger the image view area (A) and capture antibody surface density (b), the more binding events can be detected and the smaller of the error will be. However, minimizing the detection error by increasing A and b with the previously reported method faces technical limitations for reasons discussed below.

One useful technique for increasing A is to decrease the magnification. This will lower its capability to resolve nanoparticles because of two reasons:

First, shot noise will be greater. The shot noise is associated with the finite number of photons detected by an image sensor (CMOS or CCD). A low magnification image captures a wide view of the sensor surface, but each nanoparticle in the image falls on a smaller number of pixels on the imager. Each pixel can only detect a certain number of photons per image frame before saturation, the total number of pixels used to detect each nanoparticle is thus limited. The method and system disclosed herein overcomes this shot noise limit by maximizing illumination light intensity and integrating signals from the individual pixels over sufficient time.

Second, low magnification usually means lower spatial resolution (smaller numerical aperture used for low magnification imaging), which makes it impossible to resolve nanoparticles located on the sensor surface within the spatial resolution. Increasing the capture antibody surface density (b) faces the same spatial resolution limitation. For example, if b is too large, such that the average distance between two binding sites on the sensor surface is smaller than the optical spatial resolution, then two nanoparticles bind to two adjacent capture antibody molecules cannot be resolved. The method and system disclosed herein overcomes this issue with a real-time single nanoparticle detection scheme. The scheme detects individual nanoparticle binding to the sensor surface in real time (e.g., with a time resolution of Δt). When two nanoparticles bind to a region within the spatial resolution one at a time, separated with a time interval greater than Δt, it detects two binding events without the need of spatially resolving the two nanoparticles. This real-time detection scheme has several benefits: It increases the dynamic range because it can detect more nanoparticles for a given area of the sensor surface. It minimizes errors associated with two nanoparticles closely spaced within the spatial resolution. Finally, real-time detection also helps to shorten detection time. For example, if the biomarker concentration is high, then the nanoparticles binding to the sensor surface can quickly reach a statistically sufficient number and the detection can stop promptly to save time.

Signal Processing Module

The signal processing module 1008 comprises software with the following on-line and off-line algorithms:

(1) Perform denoise on the captured images to reduce noise while maximizing signal to ensure that single nanoparticles can be imaged.

(2) Count the individual nanoparticles in real time.

(3) Determine difference (or gradient) in the counts at two (or more) locations along the fluidic channel.

(4) Relate the difference (or gradient) to the concentration of the biomarker.

(5) Evaluate the statistical variability to determine if the detection time is sufficient. For example, the relative statistical error would be $$\frac{1}{\sqrt{N1-N2}}$$

The error decreases with time. If this error decreases to the precision specified for an application, then the detection stops and a concentration together with error is provided.

Data Calibration System

The data calibration system 1018 is a computer program run by a processing system in the detection system and is adapted to correlate the difference in the number of particles on the first and second zones to the concentration of the biomarker.

Differences of the Disclosed Method and System from Previous Arts:

Comparison with Lateral Flow Immunoassay Stripes

The lateral flow immunoassay stripes are made of paper. It includes a sampling pad for introduction of a fluidic sample, which conjugates with gold nanoparticles, flows along the strip to a region with capture antibody. The binding of the biomarker conjugated gold nanoparticles produces a color change visible by eye. The lateral flow immunoassay often includes an internal reference region to ensure successful test.

The method and system disclosed herein are different from the lateral flow immunoassay in several major ways. First, in contrast to the lateral flow immunoassay strips, the present invention features detection of single binding events, which is digital detection, leading to dramatically improvement in the detection limit, dynamic range and quantification capability (rather than a qualitative positive or negative answers). Second, the detection reads and counts single nanoparticles (rather a color change) with an imaging system and algorithm. Third, it features internal reference enabled by detection and comparison of binding events along the fluidic channels. This internal reference or calibration is a key to achieve high precision required for many acute disease diagnosis and treatment Comparison with the Microwell-Based Digital Immunoassay As currently known, a microwell-based digital immunoassay uses an array of microwell, each performs ELISA with enzymatic amplification[3]. For sufficient low concentration biomarker samples, each microwell has either zero or one biomarker molecule. Enzymatic reactions in the microwell with a single biomarker leads to a fluorescence signal, which is detected as one.

The method and system disclosed herein has a number of major differences from the microwell method. For example, it does not use microwell nor use signal amplification based on enzymatic reactions or fluorescent detection, which thus reduces the need of fabricating an array of microwells, and reagents for enzymatic reaction and fluorescence detection. Further, it detects the biomarker either directly or via a detection antibody-conjugated nanoparticle, rather than detecting signal from each microwell. If the opening area of microwell is denoted with $A_{microwell}$, and total sensor surface area as $A_{total}$, the dynamic range is $A_{total}/A_{microwell}$. In the method and system disclosed herein, the dynamic range is $A_{total}/A_{nanoparticle}$, where $A_{nanoparticle}$ is the area of a nanoparticle ($pi*D^2/4$, where D is the diameter of the nanoparticle). Because of the size of the nanoparticles is much smaller than the size of the microwell, the method and system disclosed herein can reach single molecule detection capability, but with a large dynamic range. Further, the method and system disclosed herein features an internal reference to minimize errors and improve precision.

Comparison with Single Molecule Fluorescent/Flow Cytometry Digital Immunoassay

As currently used, flow cytometry flows a sample across a laser beam, and binding of a biomarker molecule to an-antibody leads to a fluorescent signal, which is detected as a biomarker[5]. The detection in this method is sequential because it detects one molecule at a given time, which is slow. This method also lacks internal reference, which leads to precision concerns.

The method and system disclosed here significantly differs from the flow cytometry-based method. For example, it images multiple binding events (nanoparticles) in parallel, which shorten the detection time. As a further example, it has an internal reference using difference detection to minimize errors.

Comparison with Nanoparticle Enhanced Reading of ELISA

Nanoparticles have been used to enhance a binding signal, but most technologies detect a layer of nanoparticles, rather than single nanoparticles[6-8]. Single nanoparticle detection provides improved detection limits. To date, two types of single molecule detection schemes have been proposed. One is based on dark field optical microscopy, which detects scattered light from the individual nanoparticles. For metal nanoparticles, plasmonic resonance leads to a color of the nanoparticles. While capable, the dark field imaging technology is prone to artifacts due to impurities and non-specific adsorption. Typically, high magnification is used in the dark field method for the detection of nanoparticles[12]. An improved method is to use nanorods instead of nanoparticles[6].

These single nanoparticle tracking approaches suffer from several limitations. (1) Two or more nanoparticles located within a distance smaller than optical diffraction limit cannot be resolved by the static images, which will mistake the two or more nanoparticles as a single particle, and thus lead to under counting of the particles. This is especially the case for low magnification imaging that has poor spatial resolution, and high-density nanoparticles bound to the surface. (2) Nanoparticles must be separated with a distance greater than optical resolution, whose fundamental limit is optical diffraction. This will limit the number density of nanoparticles that can be detected with these technologies, which places an upper limit in the dynamic range.

The method and system disclosed herein differs from the previously disclosed technologies in several ways. For example, it features real-time tracking of single nanoparticles, so that two binding events within the spatial resolution can be detected and counted individually as long as they do not bind to the surface exactly at the same time. As a further example, the presently disclosed method uses real-time tracking thus minimizing errors due to diffraction limit and also increasing the maximum number of nanoparticles can be detected within the image view, which expands the dynamic range of the detection. As a further example, the real-time tracking of nanoparticles also enables an algorithm that determines if sufficient number of particles is detected to provide the precision needed for a particular application. As yet a further example, the method and system disclosed herein includes an internal reference to improve precision by removing non-specific adsorption and by canceling out common noise in the system.

EXAMPLES

In one example carried out by the inventors, a time-resolved digital immunoassay (TD-ELISA) technique based on plasmonic imaging of nanoparticles for rapid detection of biomarkers with a wide dynamic range was reported. It will be recognized that this is one example and the invention is not limited by any examples detailed herein. The plasmonic imaging offers high contrast and fast imaging of nanoparticles, allowing detection of single molecule binding on a sensor surface via detection of antibody-conjugated nanoparticles. It features real-time counting of the nanoparticles as they bind to the biomarker molecules, which provide accurate assessment of the biomarker concentration without the need of reaching thermal equilibrium via lengthy incubation. The real-time counting together with super-localization tracking of each nanoparticle allows resolving two binding events within a distance smaller than the diffraction limit, which enhances the dynamic range and minimizes the counting error. Using TD-ELISA, the inventors have achieved a limit of detection ~3 pg/mL, dynamic range 4-12500 pg/mL, and total detection time of 25 mins for procalcitonin (PCT), an important biomarker for sepsis[34].

TD-ELISA is based on counting of gold nanoparticles gold nanoparticles (GNPs) binding to the sensor surface. The higher concentration of a biomarker, the faster is the binding of GNPs, which means shorter detection time to reach a desired precision for concentrated biomarkers. The detection precision is given by $1/\sqrt{N}$, where N, the number of GNPs, increases with time. This provides a possibility to detect the biomarker from the time required to reach a fixed number of GNPs (which defines the precision), rather than counting the GNPs with a fixed time interval regardless of the biomarker concentration.

In TD-ELISA, binding or unbinding of individual GNP is resolved in time. The dynamic range of TD-ELISA is limited by the maximum number of GNP that can be covered on the area imaged, which is determined by the size of the GNP and the view area. If the inventors suppose GNP forms a monolayer on the sensing surface, with current view area of about 80 μm×60 μm, full coverage of 150 nm GNP lead to a maximum packing of about $2.6 \times 10^5$. This number is the dynamic range of TD-ELISA in equilibrium. Considering surface bounded GNP represents only fraction of the molecules of interest, the real dynamic range of molecule concentration could be as high as $10^7$ (see FIG. 12B, for example).

Sensitive detection of single GNPs was achieved with a plasmonic imaging platform, where a p polarized light beam with a proper incident angle from a superluminescence (SLED) diode was directed onto the sensor surface via a 60× high numerical aperture oil immersion objective to excite plasmons on the gold surface. The scattered and reflected light was collected with the same objective and imaged with a CCD camera. The time sequence of the plasmonic images captured the binding of the individual GNPs with a temporal resolution of 10 ms (frame rate=106 fps). Each GNP was revealed as a bright spot with a parabolic pattern arising from the scattering for the plasmonic wave on the sensor surface by the GNP inset 47, which provides high image contrast and facilitates accurate tracking of single GNPs[23, 24]. Using an automated imaging processing algorithm, the inventors tracked the position of each individual GNP and counted the individual GNP's binding to the surface over time, from which a standard curve of PCT was obtained for concentration calculation.

Figures 11A, 11B, 11C, 11D:
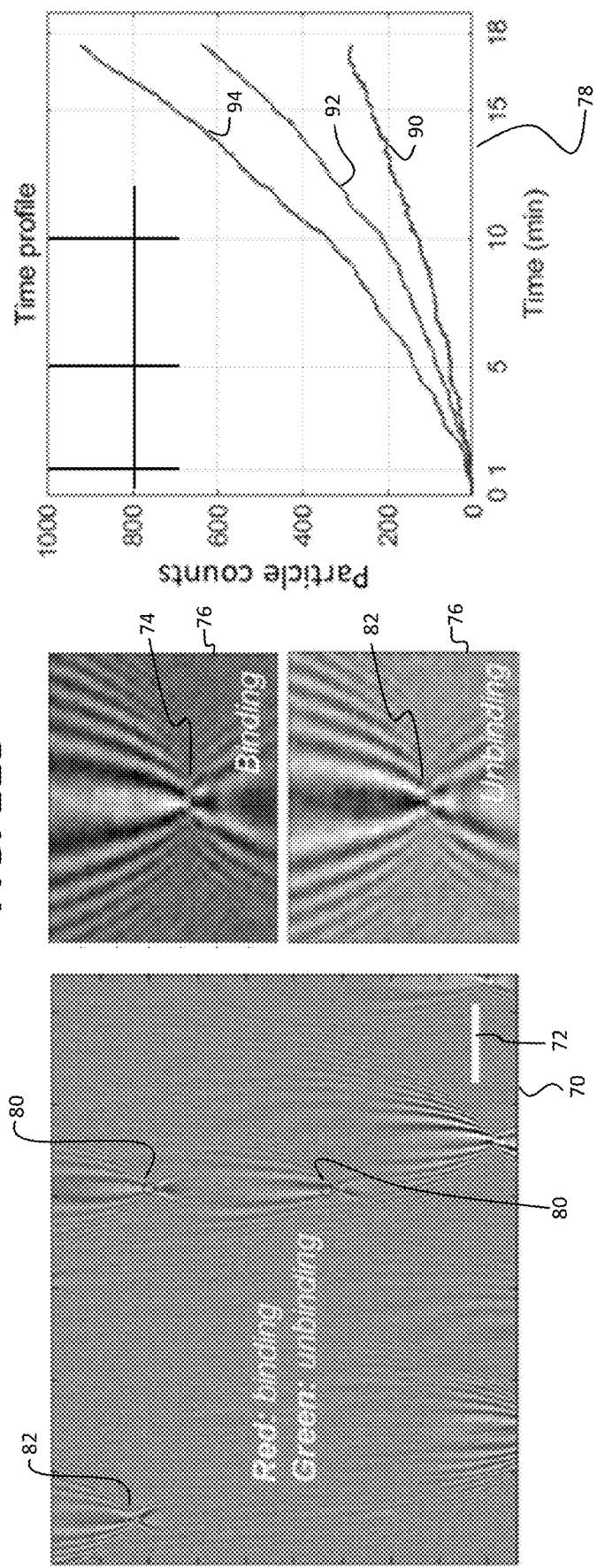
FIG. 11A schematically illustrates IgG/Anti-IgG binding quantification as represented by a typical differential plasmonic image, showing both binding and unbinding of gold nanoparticles.
FIG. 11B shows magnified images of binding gold nanoparticles, showing inverted contrast in the differential images.
FIG. 11C shows magnified images of unbinding gold nanoparticles, showing inverted contrast in the differential images.
FIG. 11D graphically represents binding, unbinding and net counts of gold nanoparticles vs. time with Anti-IgG-gold nanoparticle concentration of 50 µg/mL.

Referring now to FIG. 11A, IgG/Anti-IgG binding quantification as represented by a typical differential plasmonic image, showing both binding and unbinding of gold nanoparticles is schematically illustrated. A typical differential plasmonic image 70, shows binding and unbinding of gold nanoparticles at vertices 80, 82 each having a diameter of about 150 nm. Scale bar 72 for the image 70 is 10 μm. Binding vertices 80 may be shown as red in a color image. Unbinding vertices 82 may be shown as green in a color image.

The automated particle counting algorithm consists of following steps. First, differential images were obtained by subtracting the first image frame from the subsequent frames to generate time sequence differential images. This procedure removes common noise in the optical system and provides high contrast images of single GNPs. Second, the algorithm uses the distinct parabolic pattern of a single GNP plasmonic image as a template pattern to search and identify all the GNPs on the sensor surface with an autocorrelation pattern recognition algorithm. Because both the binding and unbinding of the GNPs take place on the sensor surface dynamically, two opposite patterns are observed for the binding (See FIG. 11B) and unbinding events (See FIG. 11C), respectively. The former is: GNP image—background, and the latter is: background—GNP image, so the images of binding and unbinding events are inverted in contrast. This allows the algorithm to differentiate and track both binding and unbinding processes over time (See FIG. 11D). Third, random noise in the image sequence is reduced by performing moving average over time. Fourth, the spatial location of each GNP was determined and tracked with a procedure described with respect to FIG. 16A and FIG. 16B below. Super-resolution fluorescent microscopy was used by Gooding et al. to track binding events within a distance smaller than the optical diffraction limit[25]. This was achieved in the present work with the dynamic tracking capability of plasmonic imaging, which can resolve multiple binding events within an area smaller than the optical diffraction limit in time domain, as long as the individual GNPs do not bind to the area at the same moment (defined by the frame rate), which improves the counting accuracy and expands the dynamic range.

Referring now to FIG. 11B, a magnified image 74 of vertices 80 illustrating binding gold nanoparticles 80 is shown as an example of inverted contrast in the differential images.

Referring now to FIG. 11C a magnified image 76 of vertices 82 illustrating unbinding gold nanoparticles is shown as an example of inverted contrast in the differential images.

Referring now to FIG. 11D binding, unbinding and net counts of gold nanoparticles vs. time with Anti-IgG-gold nanoparticle concentration of 50 µg/mL are graphically illustrated. Plot 78 graphs data comprising particle counts of gold nanoparticles against time in minutes with Anti-IgG-gold nanoparticle concentration of 50 µg/mL. Curve 94 represents binding counts. Curve 92 represents unbinding counts. Curve 90 represents net counts.

Figure 11E:
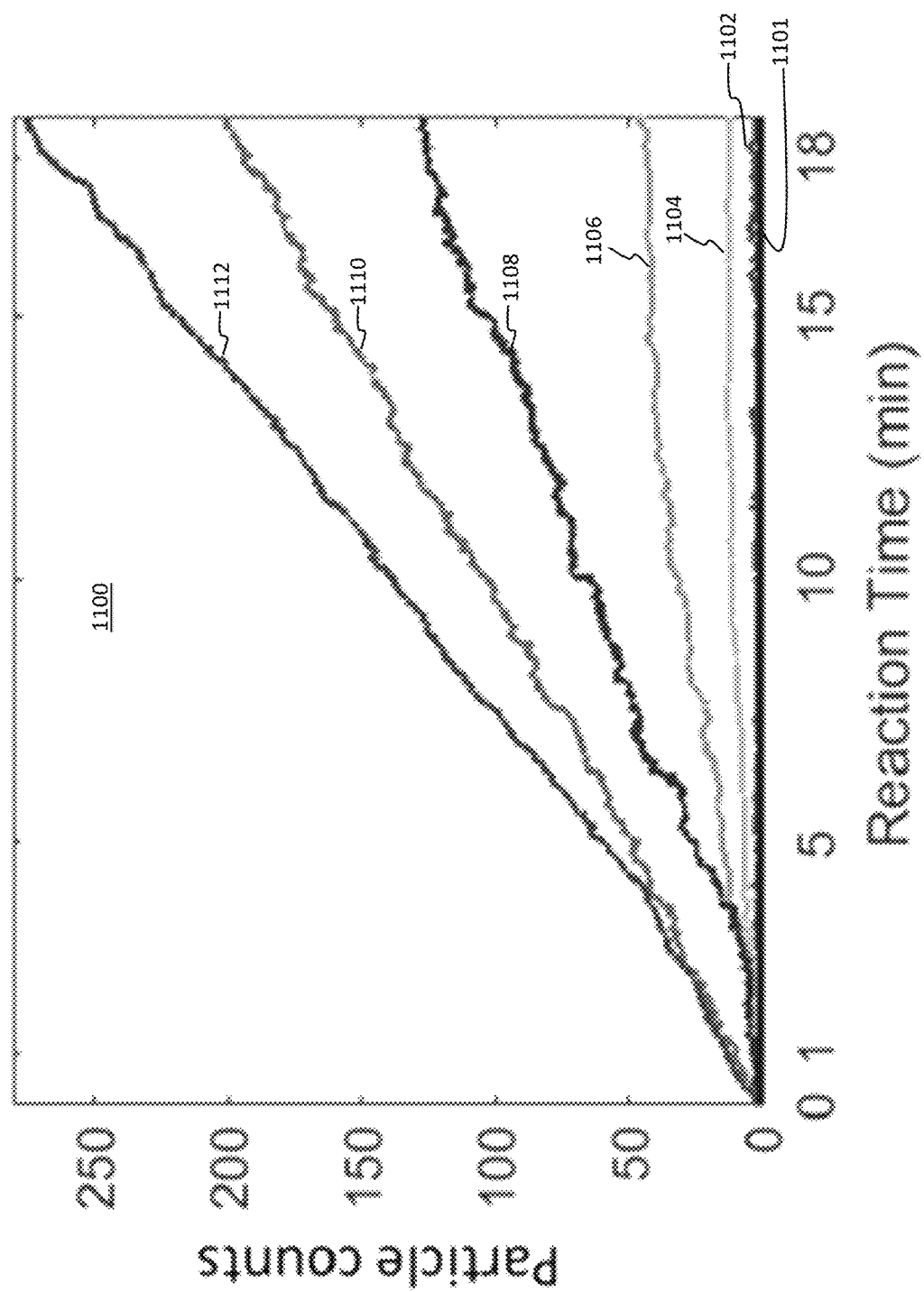
FIG. 11E graphically represents nanoparticle counts (net) vs. incubation time at different IgG concentrations.

Referring now to FIG. 11E, nanoparticle counts (net) vs. incubation time at different IgG concentrations is graphically represented. Plot 1100 is a graph of particle counts versus reaction time in minutes. A curve representing blank or absence of particles is represented by baseline 1101. Curve 1102 represents particle count over time for a sample of $5\times10^{-9}$ µg/mL. Curve 1104 represents particle count over time for a sample of $5\times10^{-7}$ µg/mL. Curve 1106 represents particle count over time for a sample of $5\times10^{-5}$ µg/mL. Curve 1108 represents particle count over time for a sample of $5\times10^{-3}$ µg/mL. Curve 1110 represents particle count over time for a sample of $5\times10^{-1}$ µg/mL. Curve 1112 represents particle count over time for a sample of $5\times10^{1}$ µg/mL.

Figure 11F:
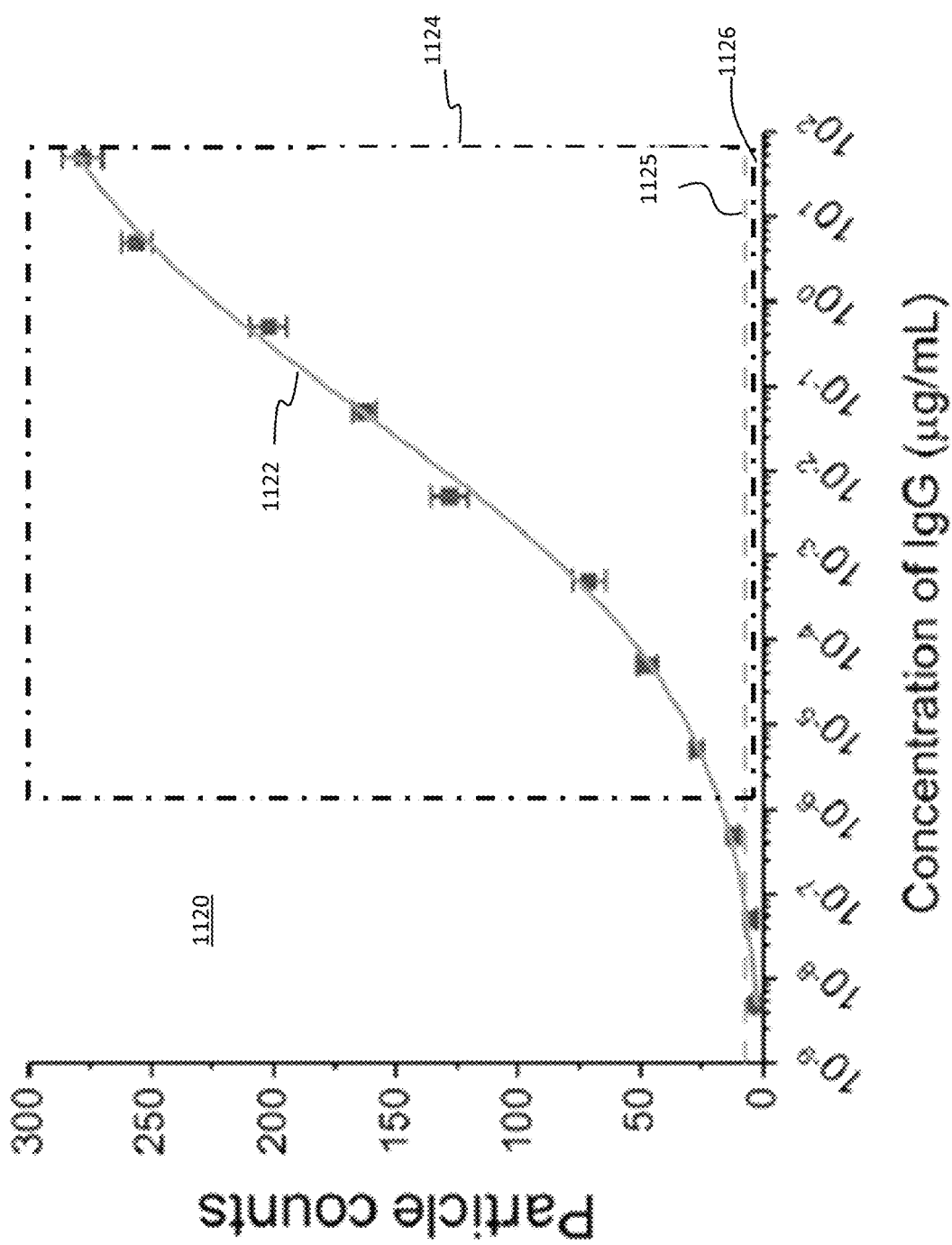
FIG. 11F graphically represents a standard curve of IgG detection.

Referring now to FIG. 11F, a standard curve of IgG detection. Plot 1120 is a graph of particle counts against concentration of IgG pg/mL. The error bars are the standard deviation from triplicate tests is graphically represented. A curve 1122 is a mathematical fit to the data. The dashed horizontal line 1126 is GNP counts of blank solutions. The area 1124 marks the dynamic range.

Validation of TD-ELISA with IgG/Anti-IgG Binding

To validate the capability of TD-ELISA for detecting antigen and quantifying antigen concentration, the inventors applied the technique to study the binding of IgG binding to anti-IgG. IgG was first immobilized onto the sensor surface, followed by incubation of anti-IgG conjugated with GNPs at different concentrations and binding of the anti-IgG to the IgG on the sensor surface was tracked by counting the individual GNP binding events on the surface with a temporal resolution of ~25 ms (frame rate of 26.6 fps). The number of GNPs counted with the algorithm varies with concentration, but for each concentration it increases linearly with time (FIG. 11E). This indicates that process recorded within the time frame is far from reaching saturation of the binding sites (IgG) on the sensor surface by the GNPs, and also far from thermal equilibrium.

From the GNP counts obtained at 20 min, the inventors obtained a standard curve of IgG. The inventors repeated the experiment 3 times and found variability less than 20% for each concentration. From the standard deviation of the triplicate test, error bars were determined and marked in FIG. 11F. The limit of detection was determined by the mean concentration measured for the blank solutions plus three standard deviations[38], which is 64.6 fg/mL (or 0.43 fM, dashed line 1125). The detectable dynamic range was from 1.3 pg/mL to 50 µg/mL, covering 7 orders of magnitude. These results demonstrate the feasibility and performance of TD-ELISA.

PCT Detection

Figure 12A:
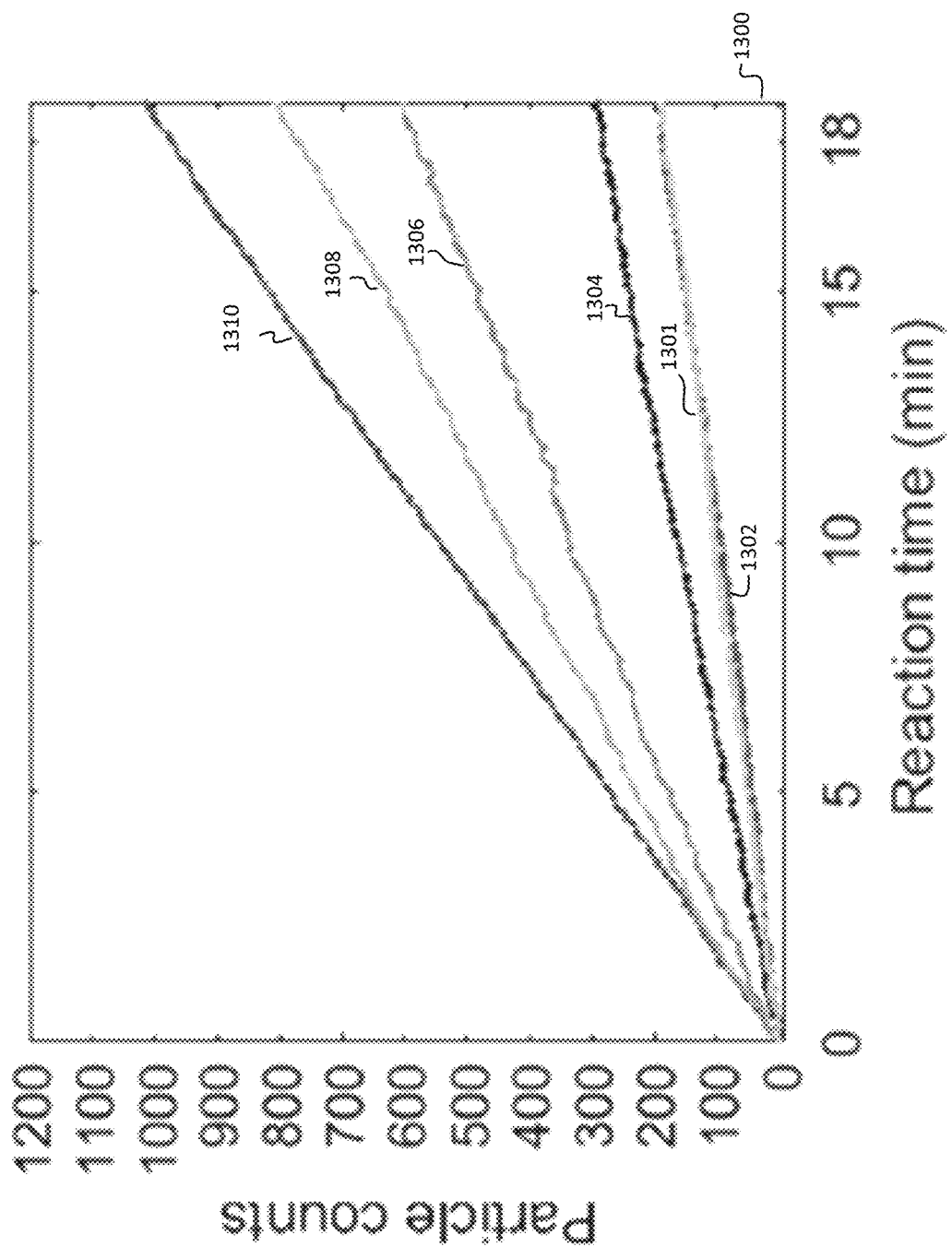
FIG. 12A graphically shows gold nanoparticle counts vs. binding time at different PCT concentrations.

Referring now to FIG. 12A, gold nanoparticle counts vs. binding time at different PCT concentrations is graphically shown. For clarity, only data of some concentrations are plotted here. Plot 1300 is a graph of particle counts versus reaction time in minutes. A curve 1301 represents blank samples or absence of particles. Curve 1302 represents particle count over time for a sample of 1.95 pg/mL. Curve 1304 represents particle count over time for a sample of 7.8 pg/mL. Curve 1306 represents particle count over time for a sample of 200 pg/mL. Curve 1308 represents particle count over time for a sample of 2000 pg/mL. Curve 1310 represents particle count over time for a sample of 12500 pg/mL.

Detection of PCT was based on sandwich assay, where a sample containing PCT was introduced and incubated for 10 min to allow binding of PCT to the capture antibody immobilized on the sensor surface. Biotinylated detection antibody was then introduced followed by introducing streptavidin-GNPs, which bind to the detection antibody via the biotin-streptavidin interaction. The binding process was tracked over time to determine the PCT concentration in each sample. FIG. 12A shows the GNP counts for different concentrations of PCT in reagent diluent buffer over 20 min captured with an imaging frame rate of 26.6 fps. The PCT concentration ranges from 0 (blank) to $1.25\times10^4$ pg/mL, which covers the concentration range of sepsis patients (0-$10^4$ pg/mL). The dynamic range of the present TD-ELISA estimated from the maximum density of GNPs is significantly higher than demonstrated here.

Figure 12B:
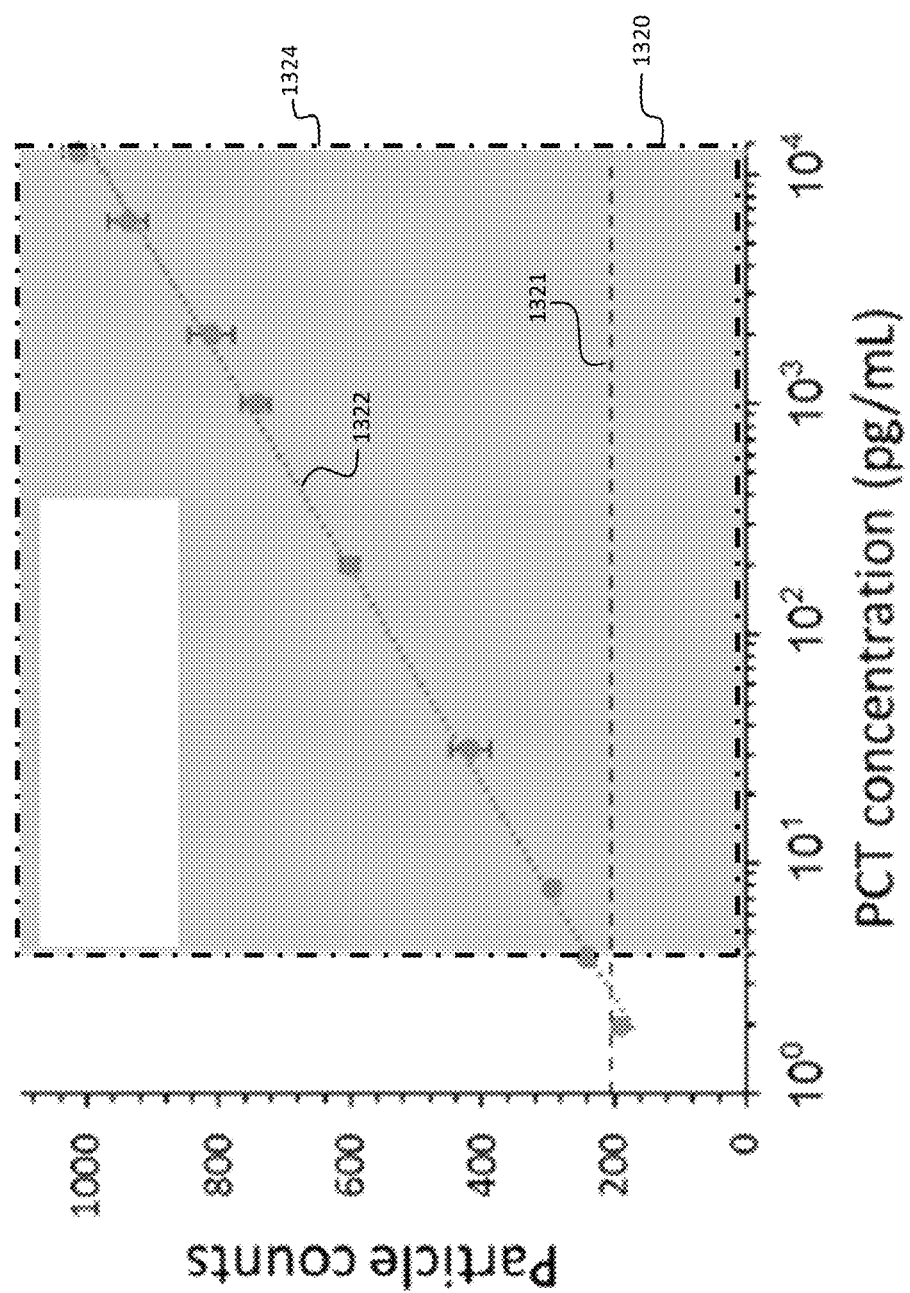
FIG. 12B graphically shows a standard curve of PCT detection.

Referring now to FIG. 12B, the standard curve of the PCT test at the 20-minute time point, showing a linear response of 5 logs ranging from 4 pg/mL to $1.25\times10^4$ pg/mL (r-square=0.9981) is shown. The error bars in the standard curve are the standard deviations over triplicate tests. Plot 1320 is a graph of particle counts versus reaction time in minutes. A dashed horizontal line 1321 represents GNP counts of blank solutions. A curve 1322 is a fit to the equation shown below. The area 1324 marks the dynamic range. The limit of detection determined by the mean concentration measured for the blank solutions plus three times of standard deviation is 2.76 pg/mL, which is marked by the horizontal dashed line 1321. The limit of quantification defined by the mean concentration measured for the blank solutions plus ten times of the standard deviation is 4 pg/mL. This limit of detection is sufficient to cover sepsis detection, where the PCT level varies from 50 to 10000 pg/mL.

Referring now concurrently to FIG. 13A-FIG. 13D, time-resolved detection of single GNPs helps improve the dynamic range and minimizing detection error associated with the binding of multiple GNPs to an area smaller than the spatial resolution of optical imaging are shown. The inventors show below that the real-time detection also helps to optimize the detection time required to achieve a desirable detection limit and precision. The inventors studied the detection limit and precision by measuring GNP count vs. PCT concentration with GNP counting time of 1, 2, 5 and 15 min, respectively. As expected, shorter GNP counting time leads to more scattered data due to smaller number of GNPs counted, but the GNP count is proportional to the logarithm of PCT concentration in each case. To evaluate the detection limit and concentration precision, the inventors used a statistical model to determine 95% prediction intervals (marked by the first and second shaded regions in FIGS. 13A-13D). The analysis shows that the error decreases with increasing time, but the 5-min error is about the same as the 15-min error. This indicates that a 5-min GNP counting is sufficient for precise PCT quantification.

Figure 13A:
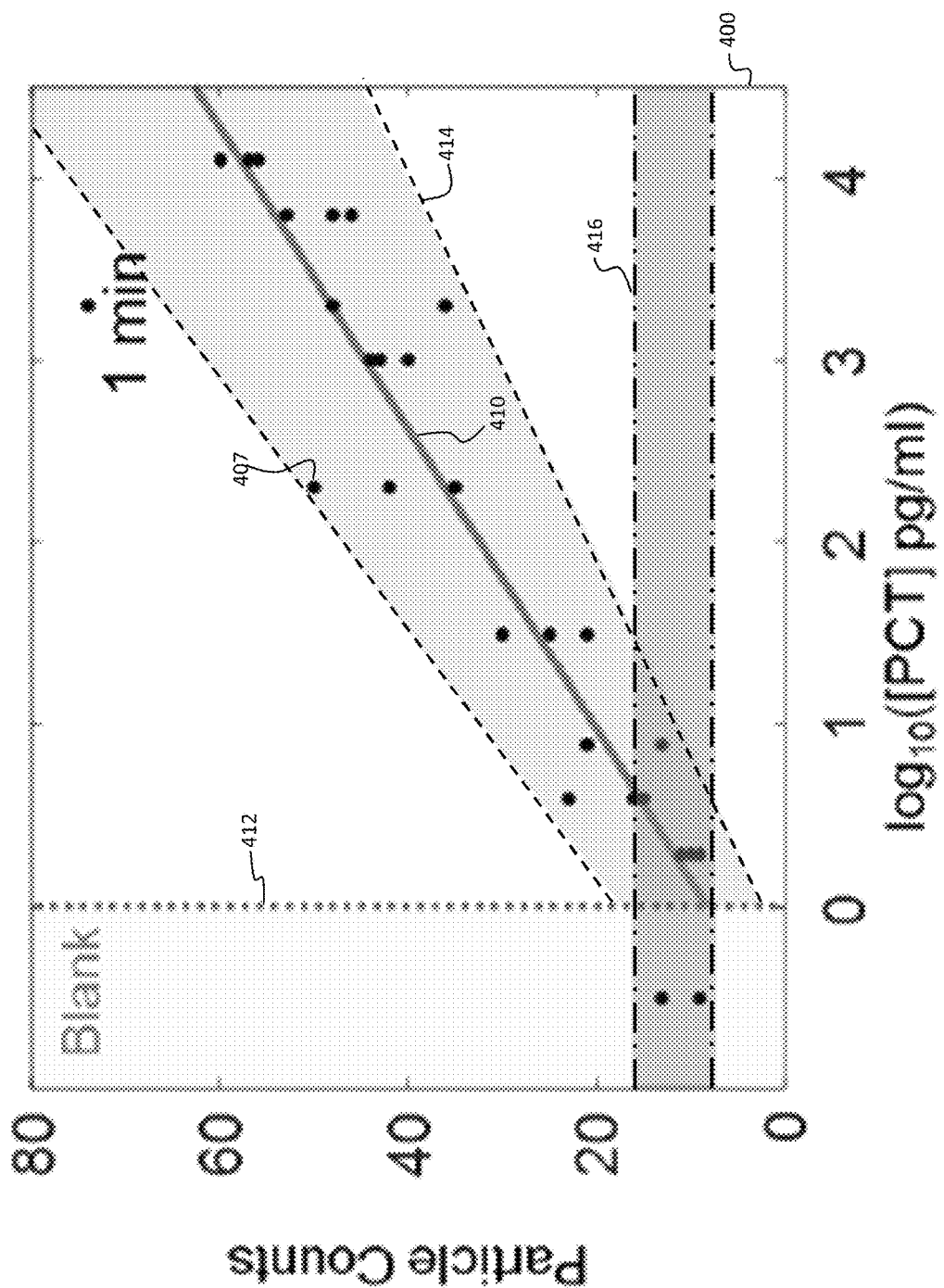
FIG. 13A-FIG. 13D show particle counts vs. PCT concentration at different counting time intervals.

Referring specifically now to FIG. 13A, particle counts vs. PCT concentration at a 1 minute counting time interval is shown. Plot 400 graphs time resolved digital immunoassay measurements of PCT at different concentrations and comparison with blank solutions for 1 minute of gold nanoparticle counting time intervals. Three replicates were carried out for each concentration and for each GNP counting time, which are shown as black dots 407. A line 412 represents blank samples having no particles. The counts of measurement are proportional to logarithm of PCT concentration, where line 410 is a linear fitting to the data, a first region 414 bracketing fitted line 410 and a second region 416 indicate 95% prediction interval according to the statistic model and measurement data. Three replicates for each concentration was carried out.

Figure 13B:
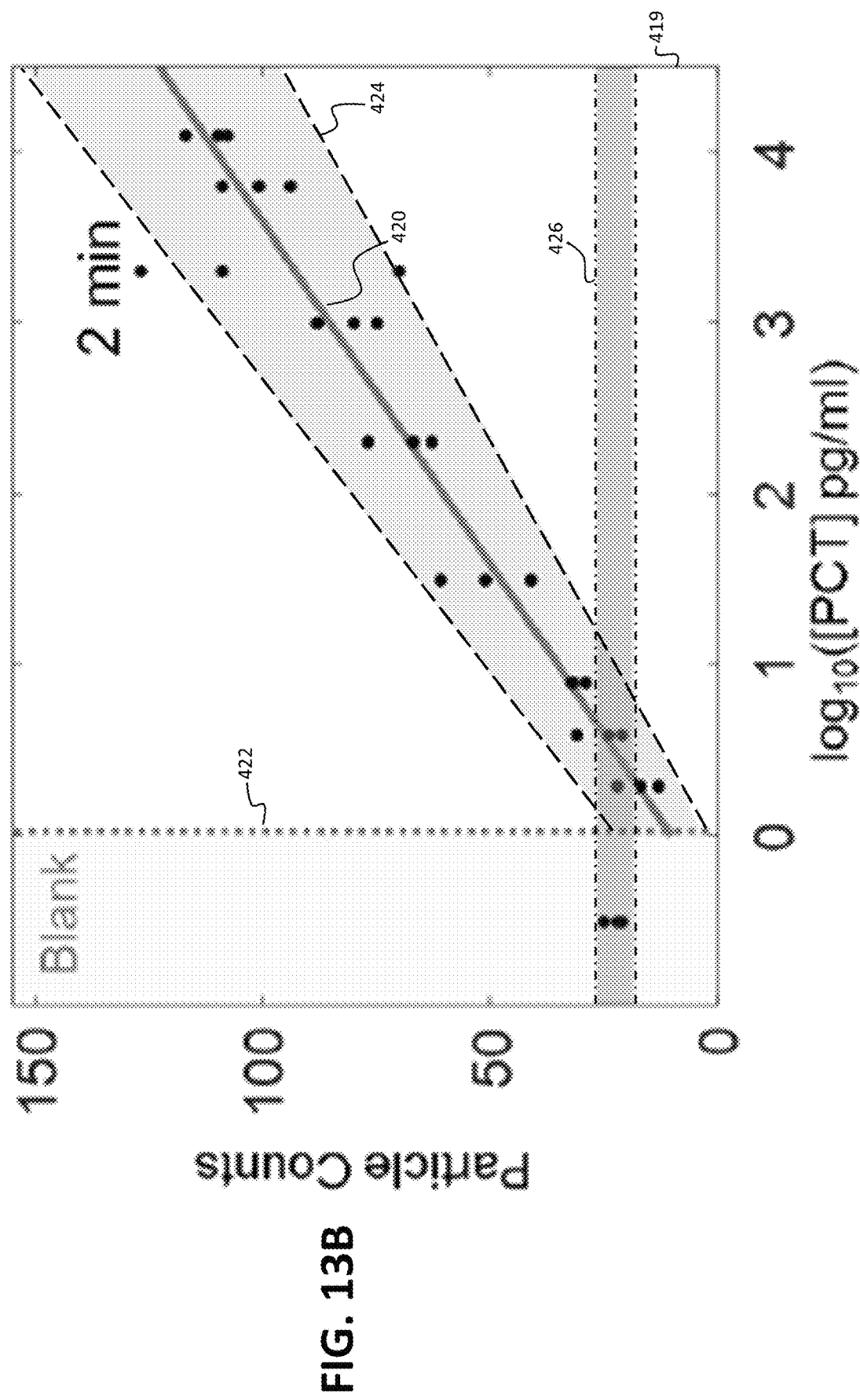

Referring specifically now to FIG. 13B, particle counts vs. PCT concentration at a 2 minute counting time interval is shown. Plot 419 graphs time resolved digital immunoassay measurements of PCT at different concentrations and comparison with blank solutions for 2 minutes of gold nanoparticle counting time intervals. A line 422 represents blank samples having no particles. The counts of measurement are proportional to logarithm of PCT concentration, where the line 420 is a linear fitting to the data, a first region 424 bracketing fitted line 420 and a second region 426 indicate 95% prediction interval according to the statistic model and measurement data. Three replicates for each concentration was carried out.

Figure 13C:
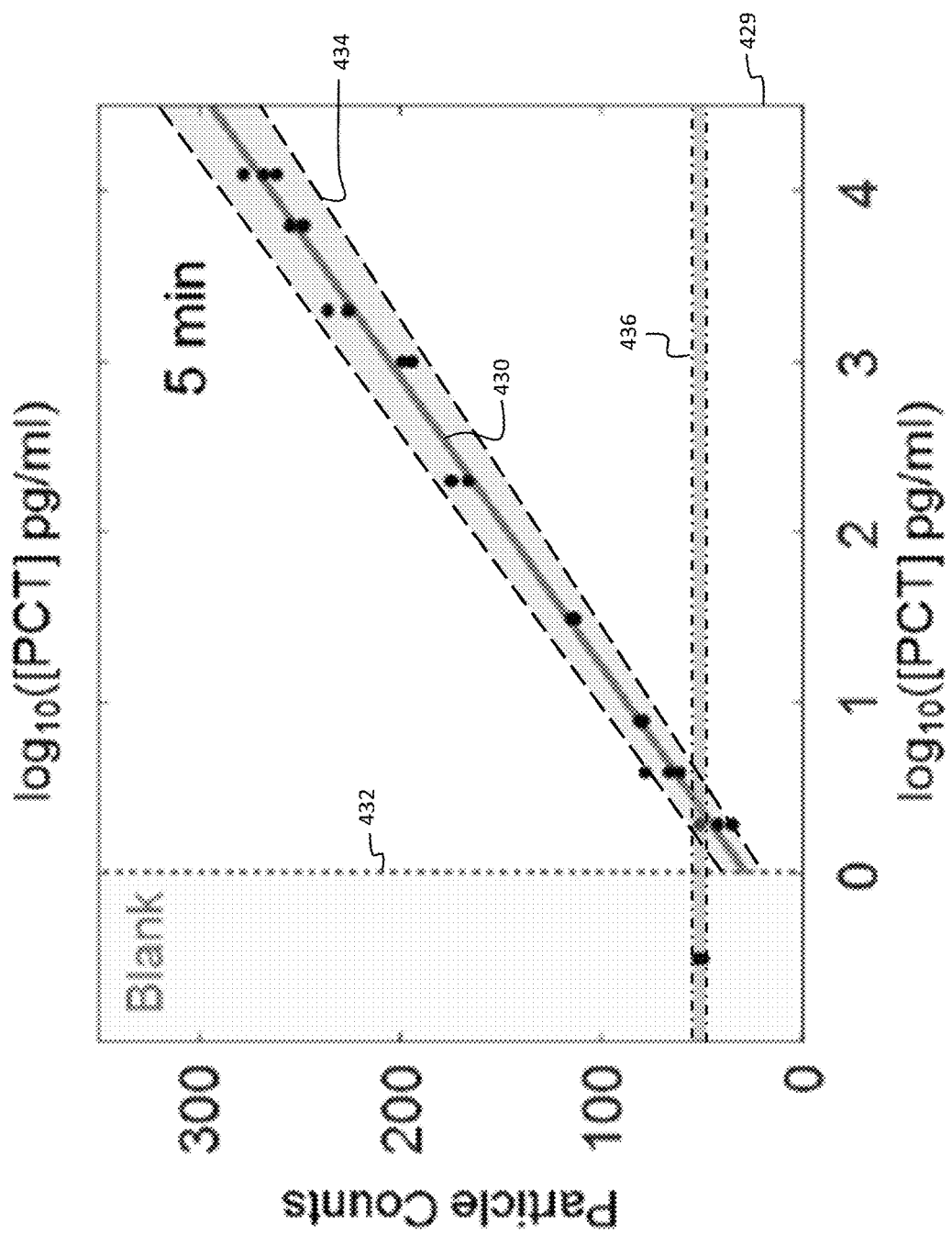

Referring specifically now to FIG. 13C, particle counts vs. PCT concentration at a 5 minute counting time interval is shown. Plot 429 graphs time resolved digital immunoassay measurements of PCT at different concentrations and comparison with blank solutions for 5 minutes of gold nanoparticle counting time intervals. A line 432 represents blank samples having no particles. The counts of measurement are proportional to logarithm of PCT concentration, where the line 430 is a linear fitting to the data, a first region 434 and a second region 436 indicate 95% prediction interval according to the statistic model and measurement data. Three replicates for each concentration was carried out.

Figure 13D:
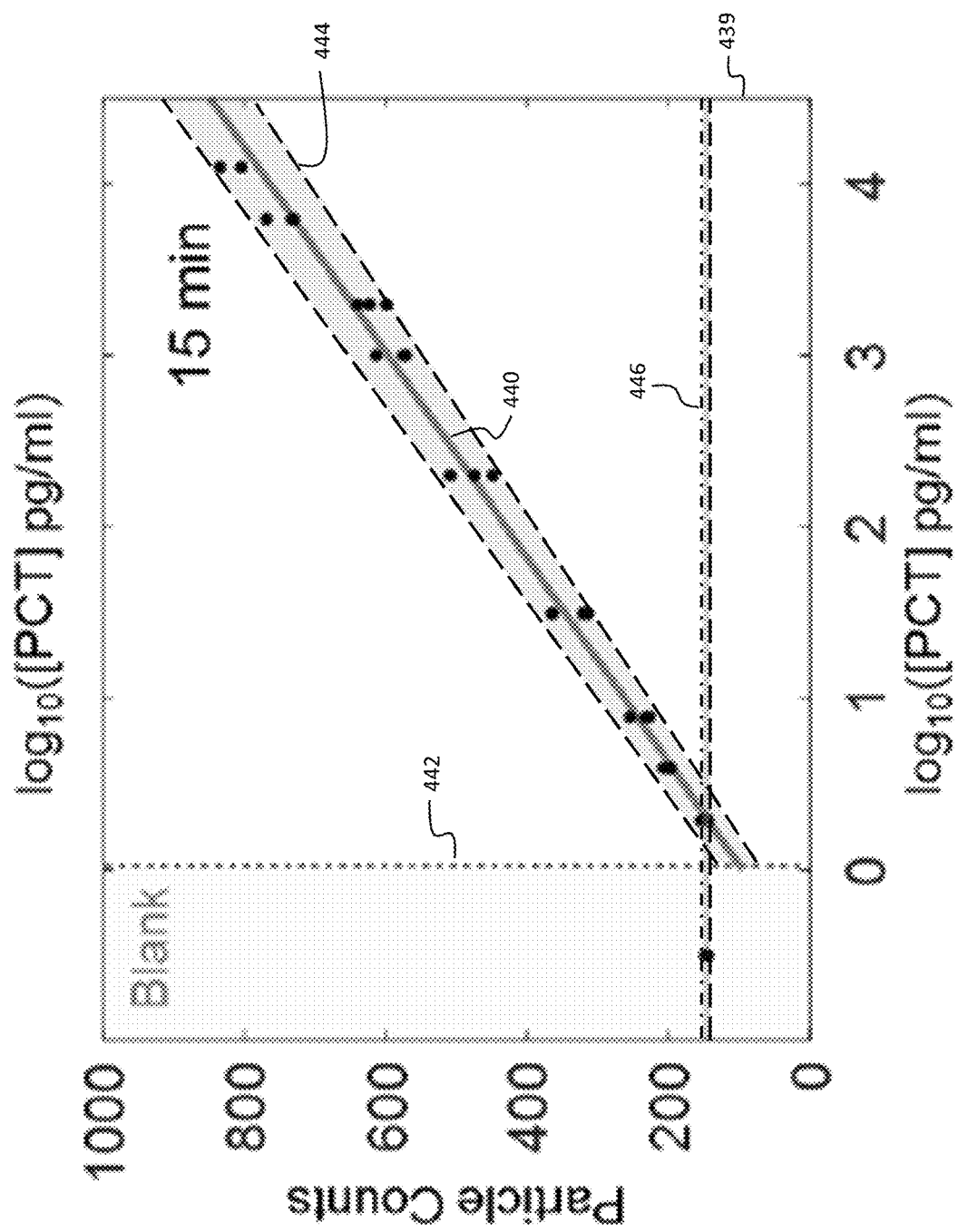

Referring specifically now to FIG. 13D, particle counts vs. PCT concentration at a 15 minute counting time interval is shown. Plot 439 graphs time resolved digital immunoassay measurements of PCT at different concentrations and comparison with blank solutions for 15 minutes of gold nanoparticle counting time intervals. A line 442 represents blank samples having no particles. The counts of measurement are proportional to logarithm of PCT concentration, where the line 440 is a linear fitting to the data, a first region 444 and a second region 446 indicate 95% prediction interval according to the statistic model and measurement data. Three replicates for each concentration was carried out.

Referring now concurrently to FIG. 14A-FIG. 14F the inventors further examined the detection limit and precision of TD-ELISA by comparing the GNP counts over time at different PCT concentrations, including blank solutions. The data shows once again that the detection limit and precision improve with GNP counting time. The data also confirms that 5 minute detection time can lead to detection of PCT concentration of 3.9 pg/mL. The inventors evaluated the limit of quantification and prediction accuracy vs. time, which shows high precision data can be obtained within 5 minutes, and longer time does not significantly improve the precision. Considering that the experiment involved 20 min incubation for PCT binding to the capture antibody and for detection antibody binding to the PCT bound to the capture antibody, the total detection time is 25 min. The detection time achieved here compares favorably with other high-performance detection techniques (Table 2) and may be further shortened by eliminating the second incubation step using detection-antibody conjugated GNPs. It is worth mentioning that the higher concentration of the biomarker the shorter the overall detection time will be. This provides a possibility of detecting a biomarker from the time required to reach a fixed precision, rather than using a fixed time interval regardless of the biomarker concentration.

Figure 14A:
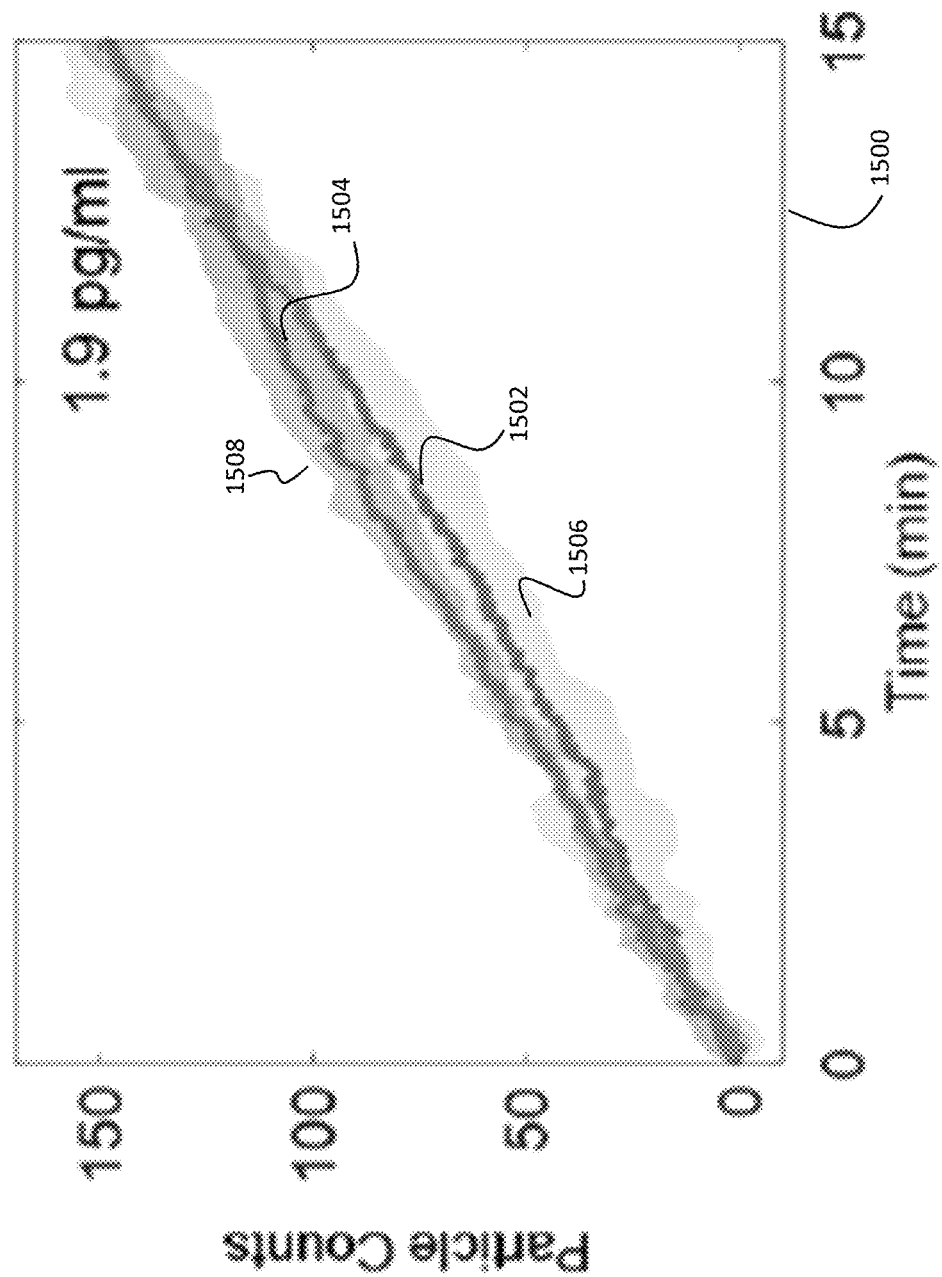
FIG. 14A-14D show particle counts vs. counting time at different PCT concentrations.

Referring specifically now to FIG. 14A, there shown is a plot of time resolved digital immunoassay measurements of PCT at concentration of 1.9 pg/ml, where curve 1502 and curve 1504 are the mean values of three replicates for PCT and blank measurements, respectively. A first shaded region 1506 and a second shaded region 1508 mark the 95% prediction interval.

Figure 14B:
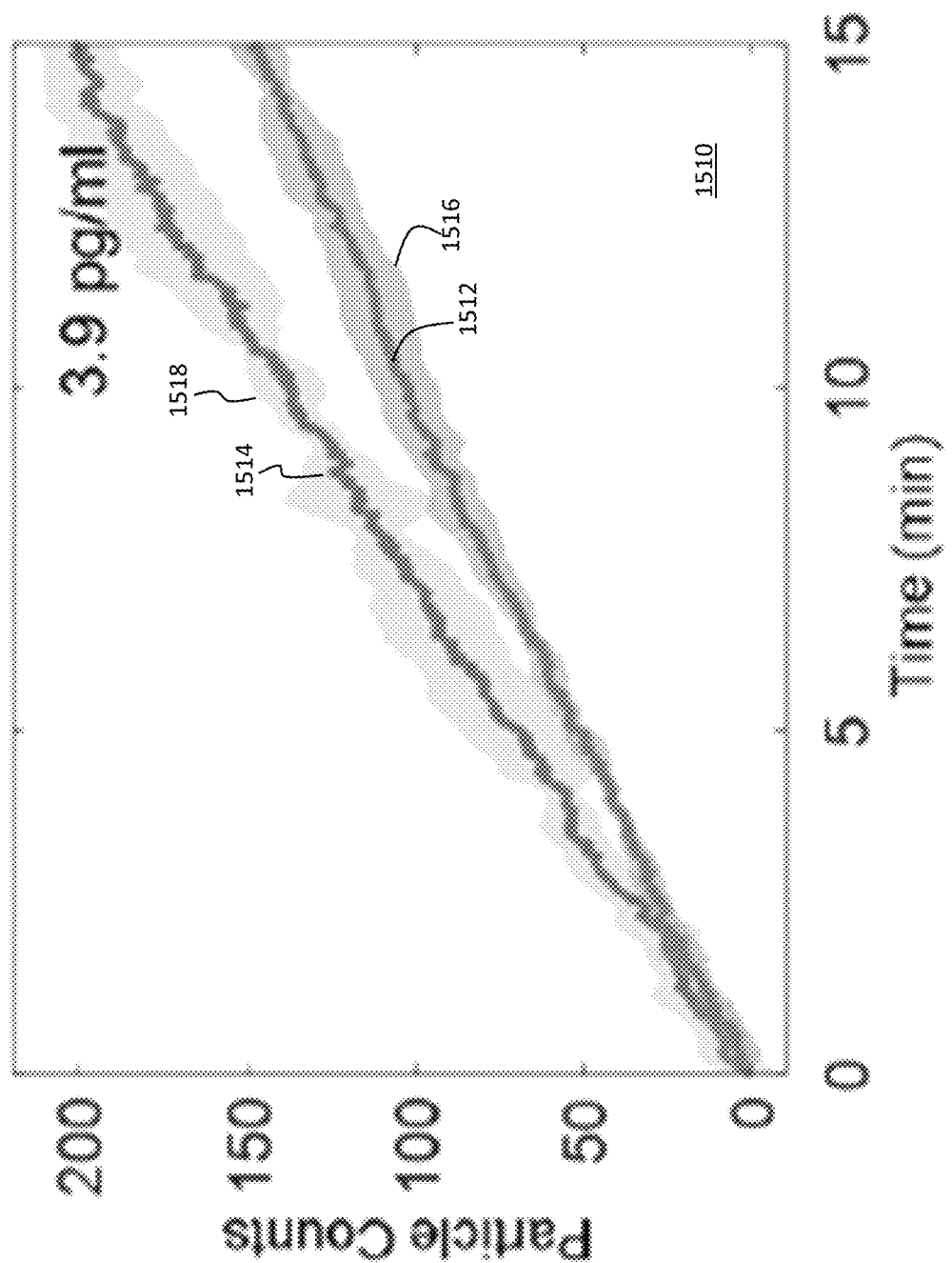

Referring specifically now to FIG. 14B, there shown is a plot of time resolved digital immunoassay measurements of PCT at concentration of 3.9 pg/ml, where curve 1514 and curve 1512 are the mean values of three replicates for PCT and blank measurements, respectively. A first shaded region 1516 and a second shaded region 1518 mark the 95% prediction interval.

Figure 14C:
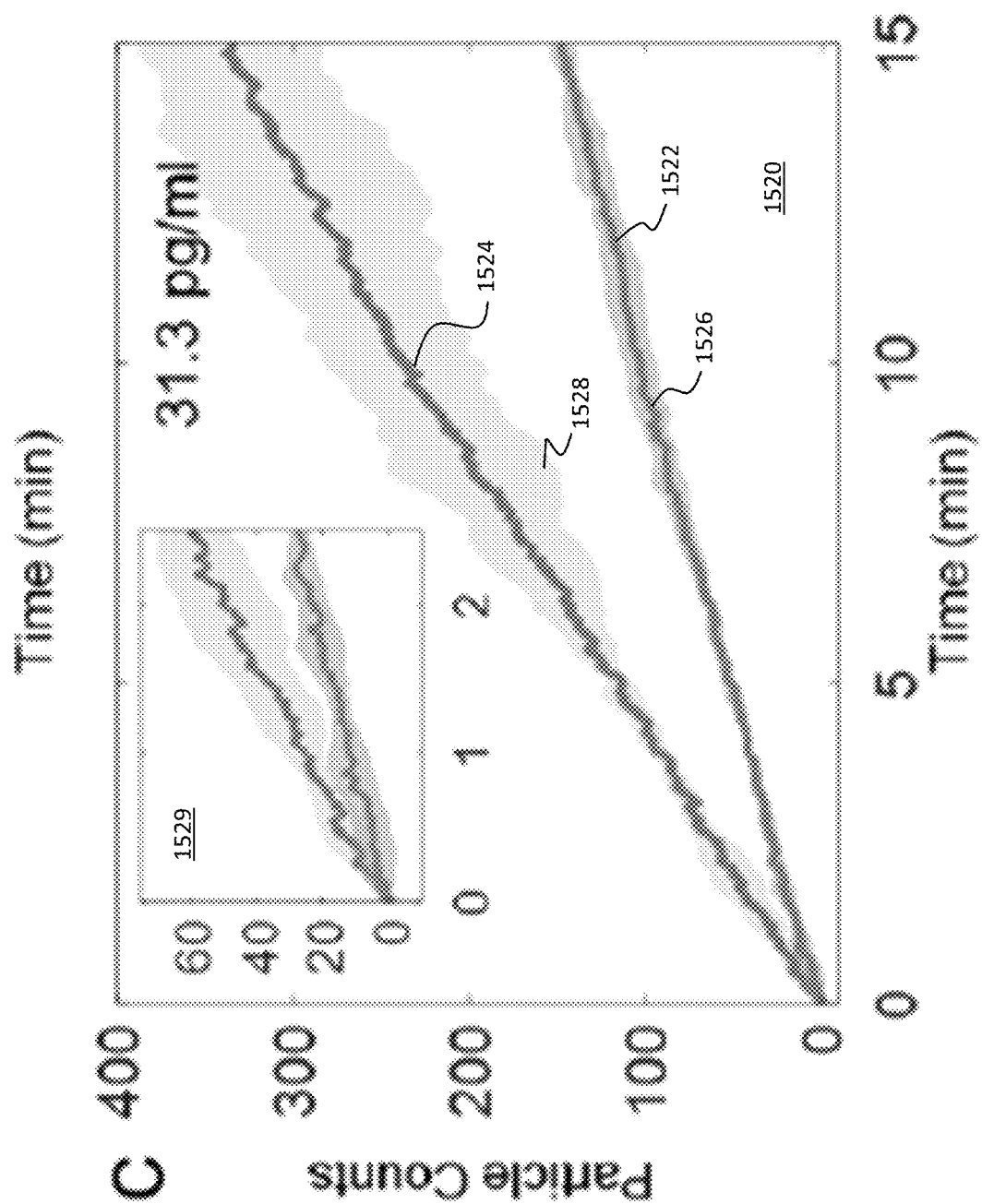

Referring specifically now to FIG. 14C, there shown is a plot of time resolved digital immunoassay measurements of PCT at concentration of 31.3 pg/ml, where curve 1524 and curve 1522 are the mean values of three replicates for PCT and blank measurements, respectively. A first shaded region 1526 and a second shaded region 1528 mark the 95% prediction interval. Inset 1529 is an expanded plot for time intervals of 2.5 min at 31.3 pg/mL PCT.

Figure 14D:
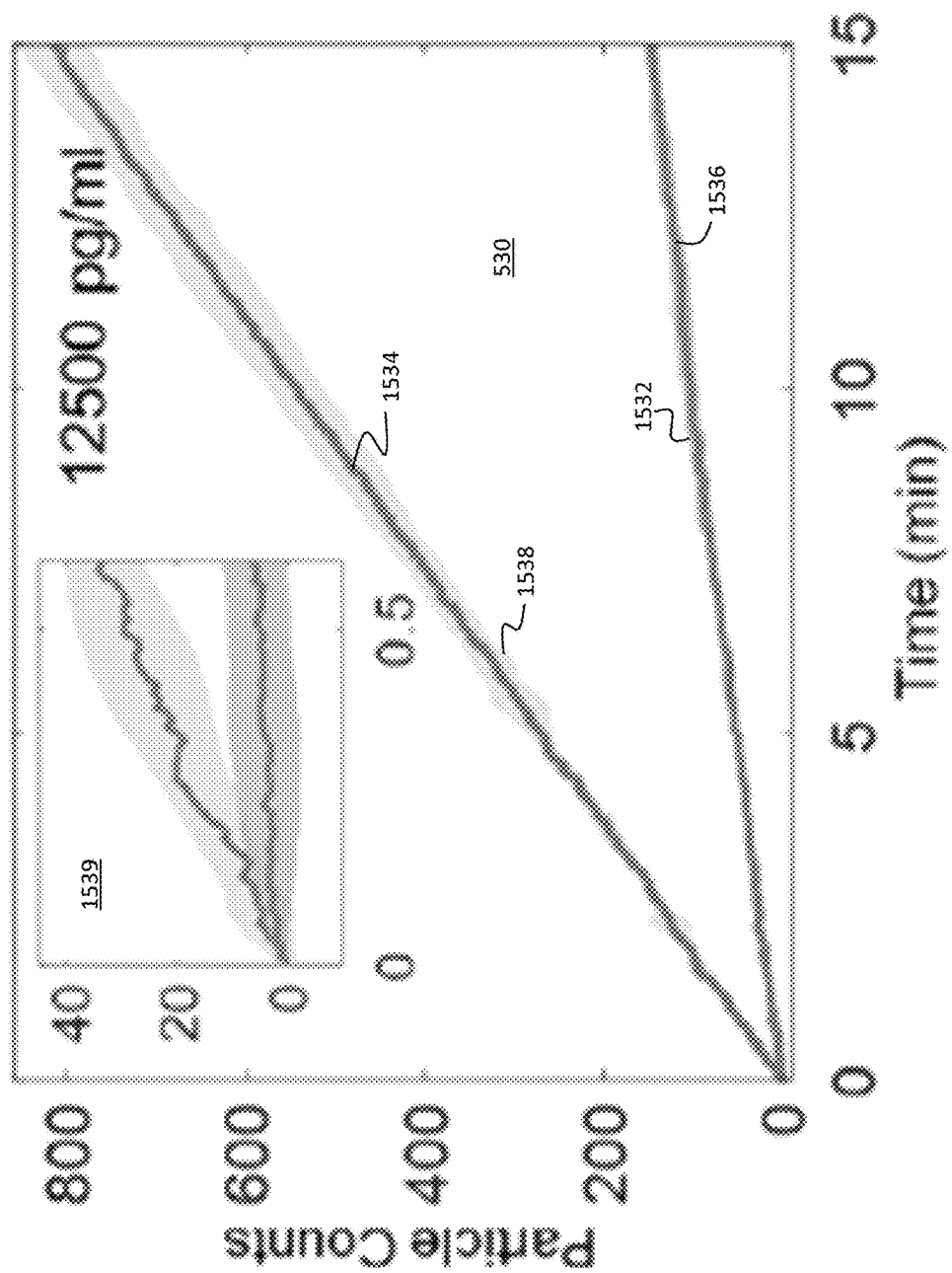

Referring specifically now to FIG. 14D, there shown is a plot of time resolved digital immunoassay measurements of PCT at concentration of 12500 pg/ml, where curve 1534 and curve 1532 are the mean values of three replicates for PCT and blank measurements, respectively. A first shaded region 1536 and a second shaded region each mark the 95% prediction interval. Inset 1539 is an expanded plot for time intervals of 2.5 min at 12500 pg/mL PCT.

Figure 14E:
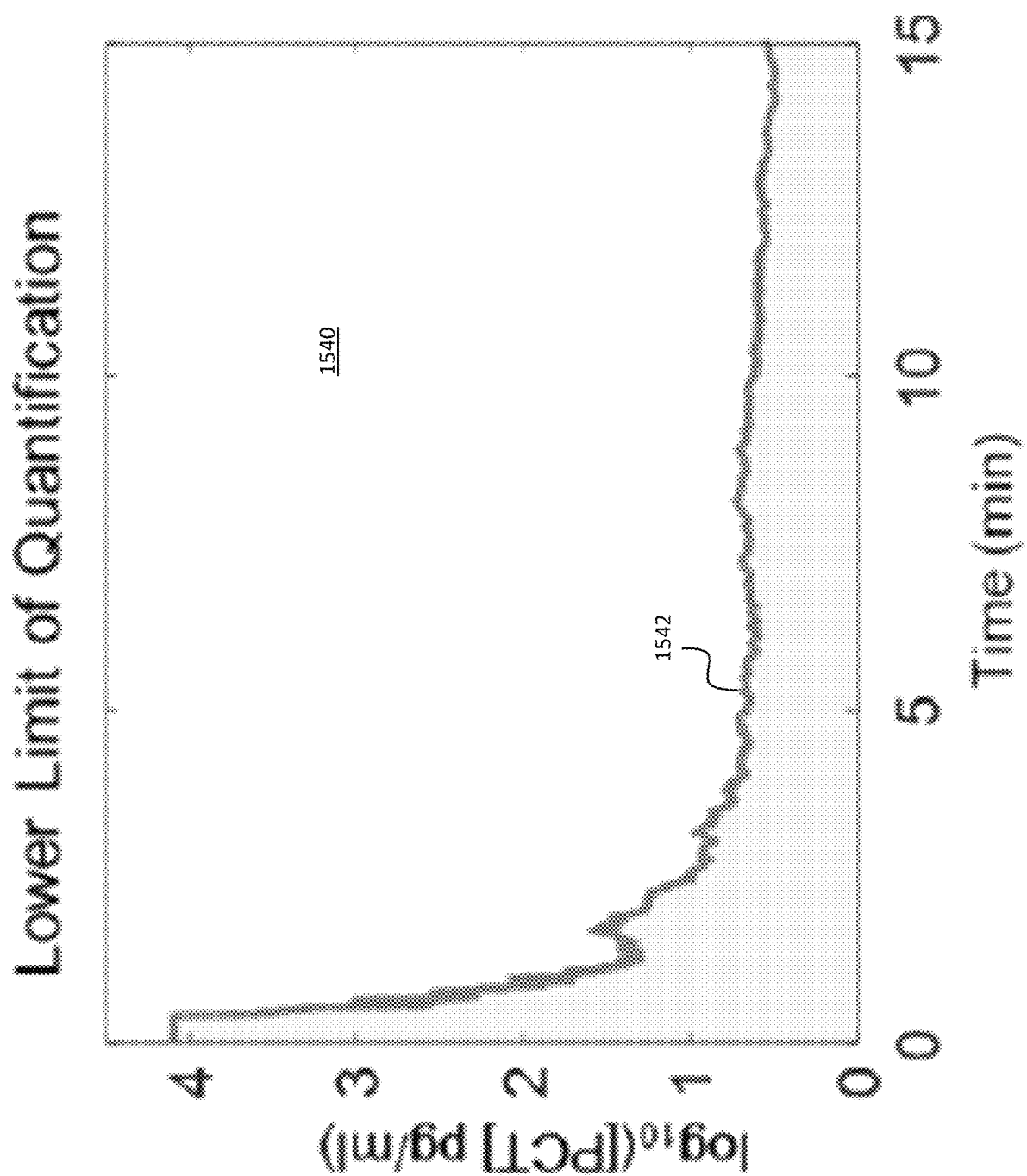
FIG. 14E graphically illustrates time dependence of lower limit of quantification.

Referring specifically now to FIG. 14E, time dependence of lower limit of quantification is graphically illustrated. Plot 1540 illustrates a lower limit of quantification. Logarithmic curve 1542 plots PCT as a function of time in minutes.

Figure 14F:
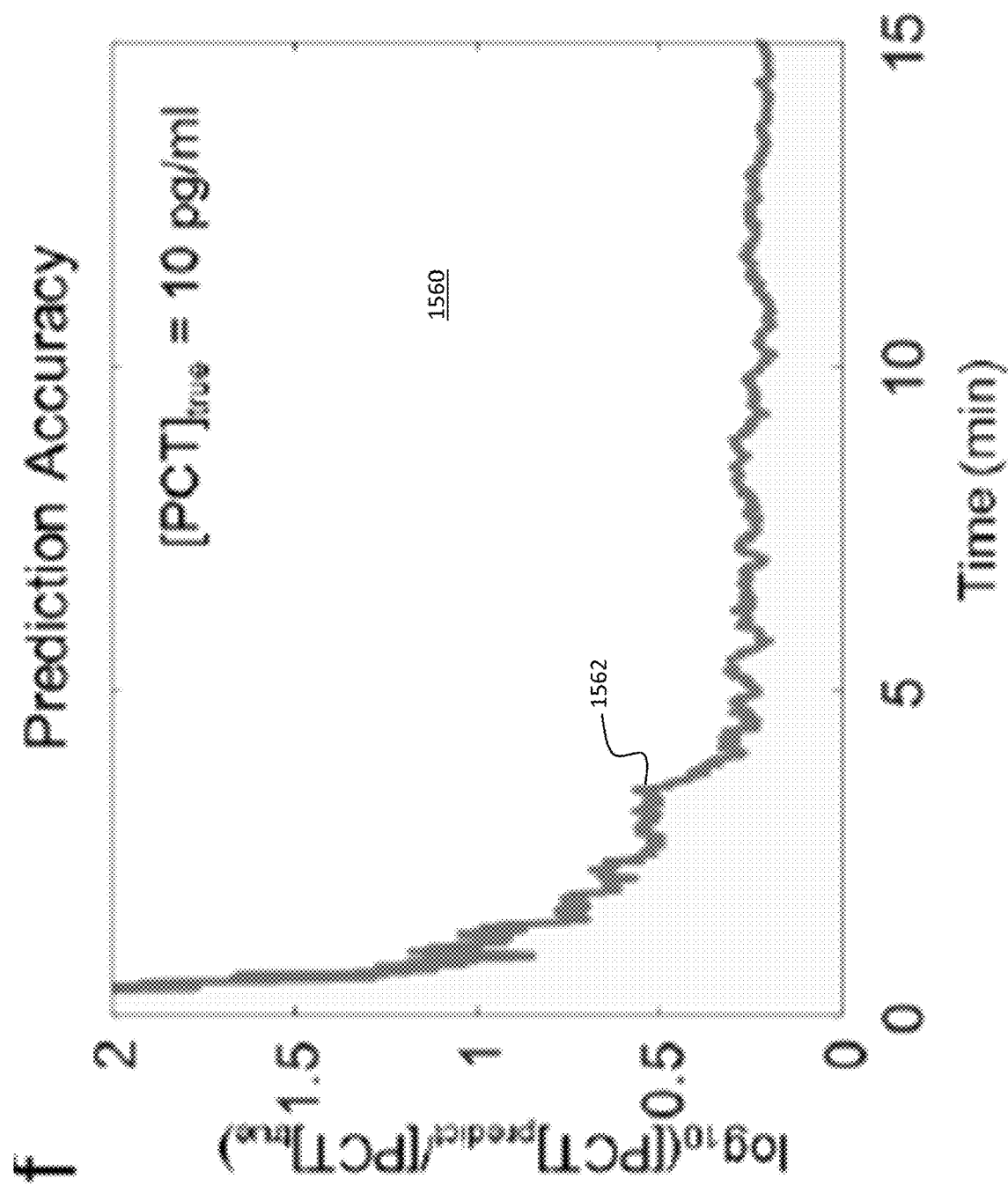
FIG. 14F graphically shows time dependence of prediction accuracy for PCT time resolved digital immunoassay measurements.

Referring specifically now to FIG. 14F, time dependence of prediction accuracy for PCT time resolved digital immunoassay measurements is graphically shown. Plot 1560 illustrates a prediction accuracy. Logarithmic curve 1562 plots a ratio of predicted PCT and true PCT as a function of time in minutes. For this measurement, [PCT] true=10 pg/ml.

Materials and Methods

Chemicals.

The following chemicals were used in the examples described herein. N-hydroxysuccinimide (NHS), N-ethyl-N'-(3-dimethylaminopropyl) carbodiimide hydrochloride (EDC), sodium acetate (NaOAc), acetic acid (AcOH), Tween 20, rabbit Immunoglobulin G (IgG) and Bovine serum albumin (BSA) were purchased from Sigma-Aldrich (St. Louis, Mo.). 150 nm gold nanoparticles coated with goat anti-rabbit IgG (011-150-TGARG-50), and 150 nm gold nanoparticles coated with streptavidin (011-150-TS-DIH-50) were synthesized by Nanopartz™. Dithiolalkanearomatic-PEG3-OH (Dithiol-PEG-OH) and dithiolalkanearomatic-PEG6-COOH (Dithiol-PEG-COOH) were purchased from SensoPath Technologies (Bozeman, Mont.). Human procalcitonin (PCT) ELISA kit (CATALOG NUMBER: dy8350-05), and DuoSet® ancillary reagent kit 2 (catalog number: DY008) were purchased from R&D system, USA. Human serum (from human male AB plasma, USA origin, sterile-filtered) was purchased from Sigma-Aldrich, USA. The kits and reagents mentioned above were accurately sub-packed and stored according to the requirement of instructions.

Plasmonic Imaging.

Plasmonic imaging was implemented on an inverted optical microscope (IX-81, Olympus, Shinjuku, Tokyo, Japan) with a 60× high numerical aperture (NA 1.49) oil immersion objective. A collimated p-polarized light beam (1 mW) from a 680 nm light-emitting diode (LED) (L7868-01, Hamamatsu, Japan) was directed onto a sensor surface via the objective to excite surface plasmons. The plasmonic images were collected by a CCD camera (Pike, F-032B, Allied Vision Technologies, Newburyport, Mass.) at a frame rage of 106 frames per second with a view area of 640×480 pixels and a pixel size of 7.4 μm. The sensors were prepared by coating BK-7 glass coverslips with 1.5-2 nm chromium and then followed by 47 nm gold. A Flexi-Perm silicone solution cell (SARSTED, Germany) was placed on top of the sensor to hold the solution. All the images were processed by using a Matlab program.

Sample Preparation.

50 μg/mL rabbit IgG solution was prepared by dissolving rabbit IgG in NaOAc/AcOH buffer (10 mM pH=5.0 NaOAc/AcOH). The solution was diluted via multiple serial dilution, 10× each, to reach different concentrations of rabbit IgG, from $5\times10^{-9}$ to 50 μg/mL. PCT capture antibody (240 μg/mL) stock solution was diluted with NaOAc/AcOH buffer (10 mM pH=5.0 NaOAc/AcOH) to reach 2 μg/mL. PCT standard was diluted with reagent diluent (solution from DuoSet® ancillary reagent kit 2) using double ratio dilution method, and the final concentration for the standard were adjusted to 12500, 6250, 2000, 1000, 200, 31.3, 7.83, 3.9, and 1.95 pg/mL. PCT spiked serum samples were prepared by diluting the PCT standard into human serum to reach 2000, 200, and 20 pg/mL. PCT detection antibody (3 μg/mL) stock solution was diluted with reagent diluent to reach a working concentration of 50.00 ng/mL. 150 nm goat anti-rabbit IgG coated gold nanoparticle solution was prepared by diluting the stock solution 1000 times with DI water and then sonicated for 5 minutes. Streptavidin coated gold nanoparticles were diluted by adding 15 μL of gold nanoparticle solution into 135 μL of PBS buffer and then sonicated for 5 min.

Sensor Surface Modification.

The sensors were cleaned with deionized water (Milli-Q, Millipore Corp.), and then ethanol, followed by hydrogen flaming. After cleaning, the sensors were immediately soaked into 1 mM of 50:1 PEG-OH/PEGCOOH mixed dithiol ethanol solution for 24 hours in the dark. The sensors were then rinsed with deionized water and ethanol and dried with nitrogen gas. Each sensor was activated for immobilization of a receptor molecule to its surface by adding 100 μL mixed 1:1 NHS and EDC aqueous solution (containing 100 mM NHS and 400 mM EDC), followed by gradient washing (gradually diluted the NHS/EDC solution by DI water).

IgG Binding to Anti-IgG.

IgG was immobilized to an activated sensor surface by incubation with 100 μL of rabbit IgG for incubation at room temperature for 10 min, followed by washing the surface with 250 μL of PBST buffer (0.05% Tween 20 in PBS buffer, Corning Cellgro) three times. Residual activated binding sites were blocked with BSA by introducing 250 μL BSA solution (1% w/v) for 5 mins and then washed with 250 μL of PBST buffer three times. 100 μL of 150 nm gold nanoparticles coated with goat anti-rabbit IgG was added, and the binding of the gold nanoparticles to IgG was tracked in real time.

Detection of PCT.

PCT capture antibody was immobilized to an activated sensor by incubation with 100 μL PCT capture antibody solution for 10 min at room temperature, followed by washing with 250 μL of PBST three times. Residual activated binding sites were blocked with BSA by introducing 250 μL of BSA solution (3% w/v) and then washed with 250 μL of PBST buffer three times. The capture antibody-functionalized sensor was either used immediately or stored at 4° C. prior to PCT assay.

Conventional ELISA Assay for PCT.

Following the manufacturer's protocol, 100 μL capture antibody was added to each well of a microplate. The well was sealed and incubated overnight, and then washed with PBST buffer three times, blocked with 300 μL reagent diluent, and incubated for at least 1 hour. The washing step was repeated three times, and then 100 μL standard or sample was added and incubated for 2 hours, followed by repeating the washing step three times. 100 μL detection antibody was added and incubated for 2 hours, and then washed three times. 100 μL of streptavidin-HRP was added and incubated for 20 minutes followed by repeating the washing step three times. 100 μL substrate solution was added and incubated for 20 minutes, and finally 50 μL stop solution was added. The optical density at 450 nm was measured using a microplate reader.

Protocol of TD-ELISA.

Figure 15A:
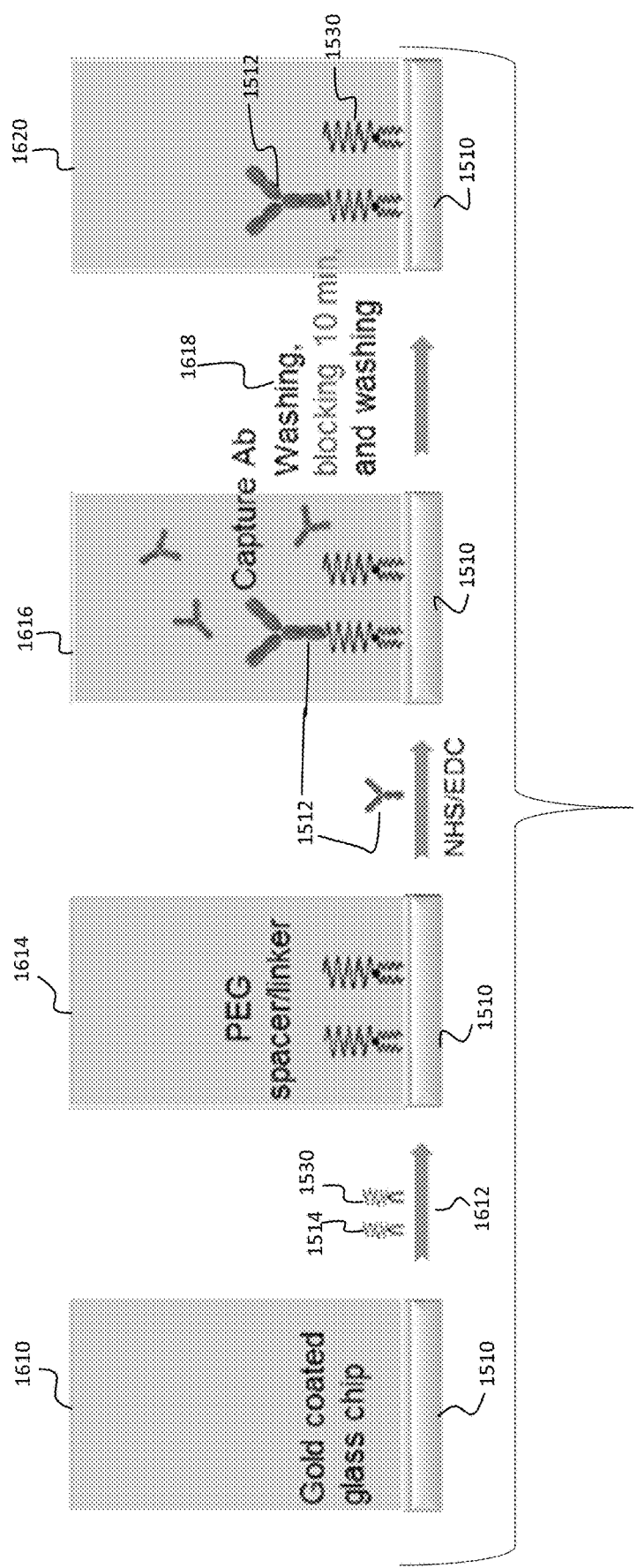
FIG. 15A schematically shows a method for preparation of capture-antibody coated sensor surface for PCT detection.
Figure 15B:
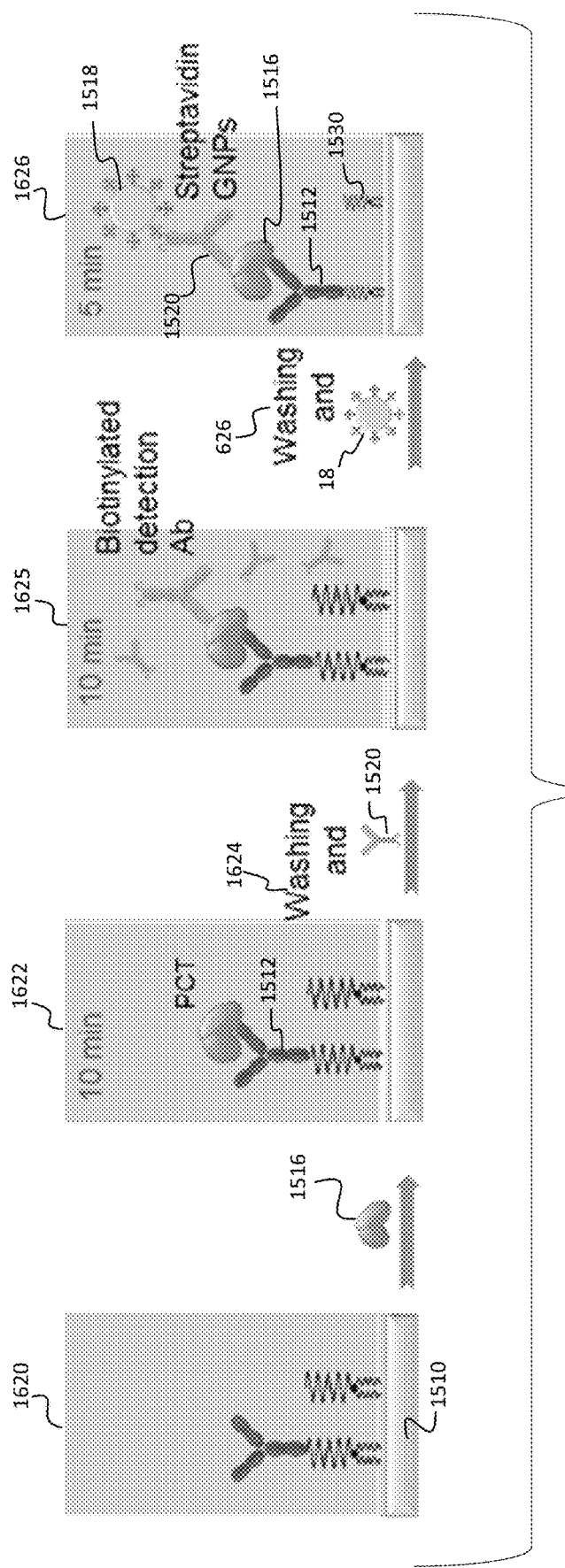
FIG. 15B schematically shows steps for the PCT assay with TD-ELISA.

Referring now jointly to FIG. 15A and FIG. 15B, a protocol for IgG binding to anti-IgG as used in the present work for PCT detection is schematically shown. The process may be initiated by obtaining a gold-coated glass chip to be used as the SPR sensor chip at stage 1610. Next a PEG linker 1514 and a PEG spacer 1530 are added at stage 1612 and affixed to the surface of the SPR sensor chip 1510 at stage 1614. Having functionalized the sensor chip, a capture antibody 1512 for procalcitonin (PCT) is immobilized by the PEG linker 1514 at stage 1616. This is followed by washing, blocking for a first time interval and washing to remove excess antibodies to produce a structure having PEG linkers with immobilized capture antibodies at stage 1620.

Now referring specifically to FIG. 15B, a sample including PCT 1516 is introduced to allow binding to the capture antibody 1512 at stage 1622. After 10 minutes the chip is washed at stage 1624. In one example as carried out by the inventors, a detection antibody, biotinylated anti-PCT antibody 20, was then added to bind with the PCT bound to the capture antibody and form a capture antibody-PCT-detection antibody complex at stage 1625. After a second similar time interval the complex is washed again at stage 1626 and a gold streptavidin coated nanoparticle (GNP) 1518 is introduced. The GNP 1518 will then bind to the anti-PCT detection antibody 1520.

In one example, the capture antibody was pre-coated on a sensor surface (gold-coated glass slide) using the steps shown. The capture antibody-coated sensor was exposed to 100 μL standard or sample and incubated for 10 min, followed by washing with PBST buffer. 100 μL biotinylated PCT detection antibody was then added and incubated for 10 min. After washing 100 μL streptavidin-coated GNP solution ($9.41\times10^8$ GNPs per well) was added (~530 streptavidin molecules are covalently coated on each GNP), during which plasmonic imaging was performed for 5 min.

Figure 16A:
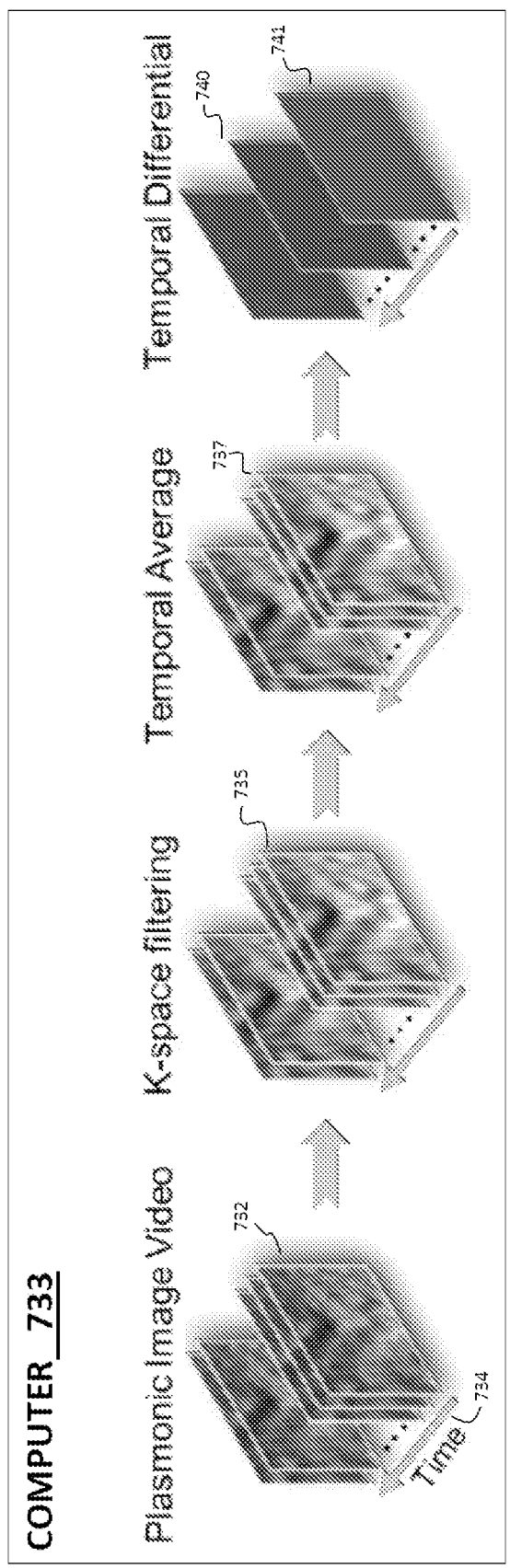
FIG. 16A schematically shows a method for implementing a particle counting algorithm on computer including pre-processing plasmonic images using K-space filtering, temporal subtraction and shot noise reduction.

Referring now to FIG. 16A, pre-processing plasmonic images using K-space filtering, temporal subtraction and shot noise reduction as utilized in an automatic particle counting algorithm implemented on a computer or equivalent digital processor is shown schematically. A more detailed example of image processing as used herein uses a plurality of raw plasmonic images 732 which are obtained over a time interval 734. Software implemented in a processor 733 applies image processing to a plurality of raw plasmonic images 732 the image processing including K-space filtering 735 and temporal averaging 737 to remove background noise by the differential imaging technique to generate a plurality of temporal differential images 740 from the plurality of raw plasmonic images 732. Each temporal differential image 741 is generated from one of the raw plasmonic images 732.

Figure 16B:
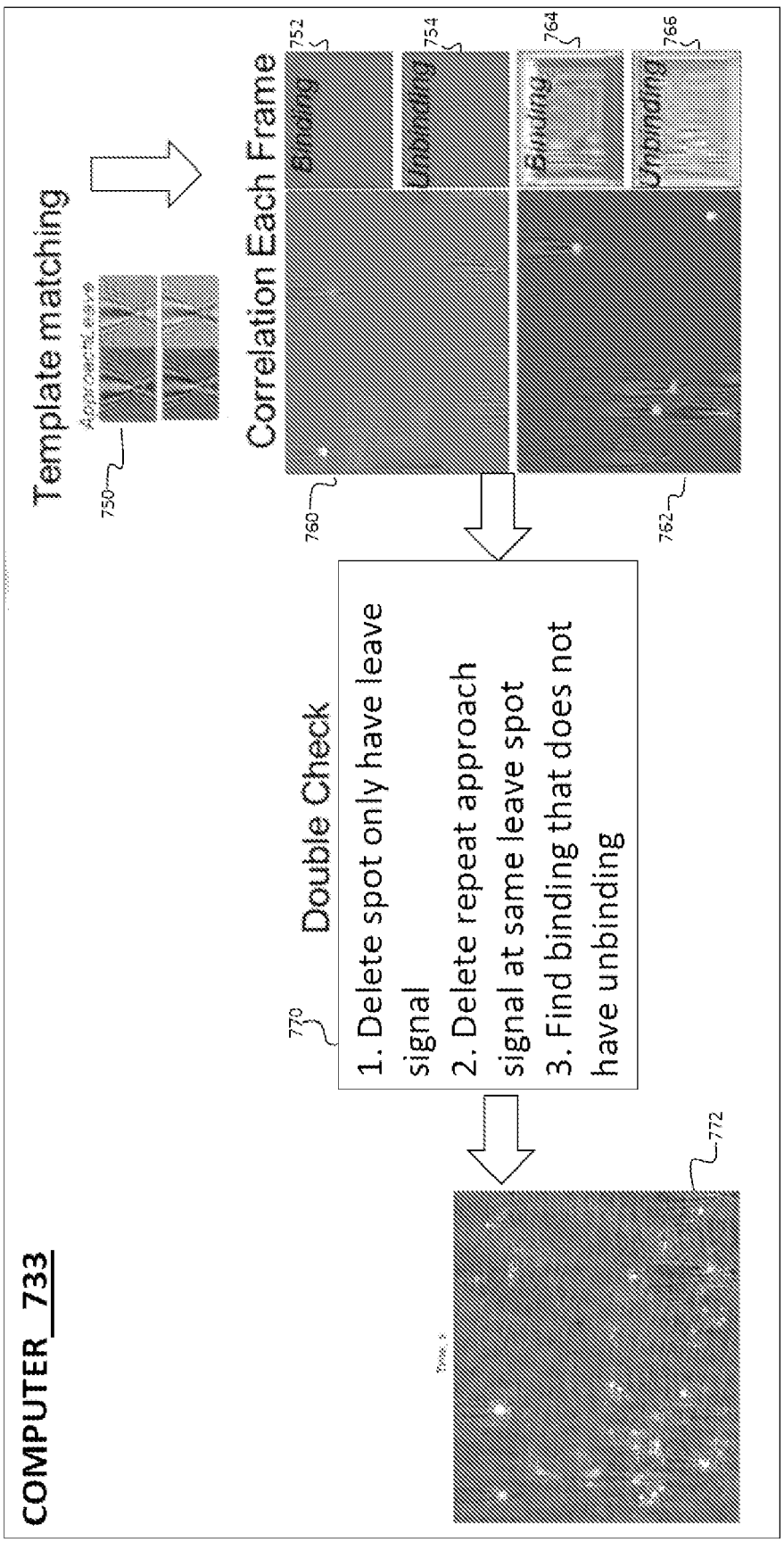
FIG. 16B schematically shows a process for identifying nanoparticles with a template-matching algorithm by detecting binding and unbinding events.

Referring now to FIG. 16B, a method for time-resolved tracking of single nanoparticles with plasmonic imaging is schematically shown. Processor 733 implements a template-matching algorithm 750. Binding and unbinding events 752, 754, 764, 766 are correlated frame by frame 760, 762. After the correlation, a double check procedure 770 including the steps of deleting spots that only have a leave signal, deleting repeat approach signal at the same leave spot and finding binding that does not have unbinding. This produced a resolved image 772 at a Times.

This procedure replaces the old way of manual counting of each nanoparticle bound on the gold surface over time which is substantially impossible because each test includes 30,000 to 130,000 frames of plasmonic images, and each frame contains a large number of nanoparticles with both binding and unbinding events taking place at the same time. An imaging-processing algorithm was developed to automatically count the binding and unbinding events using the steps shown. Step 1: Background noise was removed by subtracting the previous frame from the current frame to generate differential image sequences, and short noise was reduced by maximizing the number of photons in the differential images. Step 2: To automatically identify and count each nanoparticle in an image, a template was chosen from a pre-processed image sequence and used to correlate p with each frame. To eliminate the influence of light intensity, template matching 750 was achieved by normalizing the template and the images to be processed[3]. The binding and unbinding of nanoparticles on each image frame were determined by finding a local maximum in the correlation image. To avoid drift of the images, the algorithm automatically updated the template after a certain period of time. Occasionally, the plasmonic image of a nanoparticle was detected as fluctuating (binding and unbinding). These rare events (<0.1%) were detected but removed from counting.

Figure 16C:
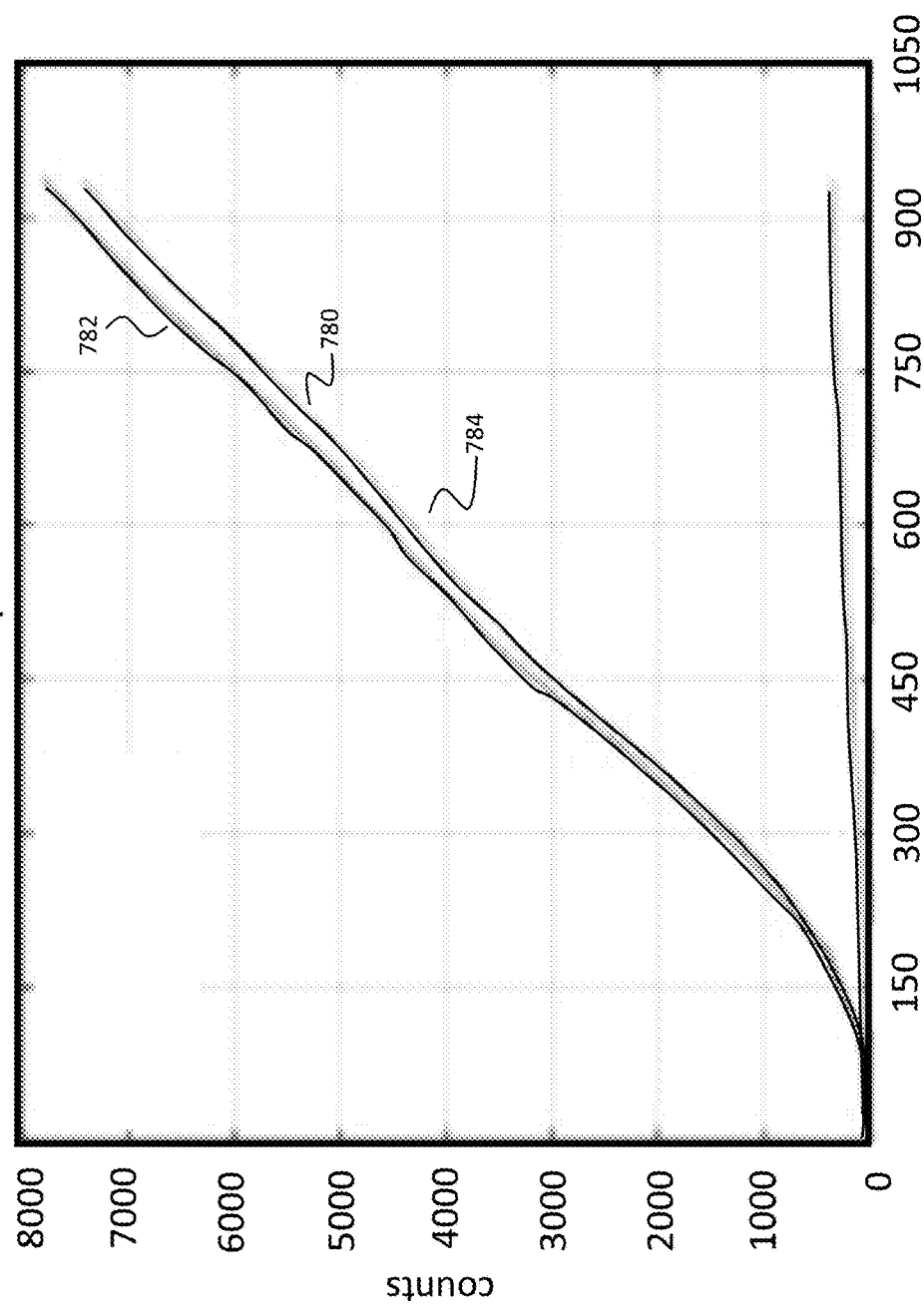
FIG. 16C graphically shows nanoparticle counting results resulting from carrying out the processes shown in FIG. 16A and FIG. 16B.

Referring now to FIG. 16C, nanoparticle counting results generated from carrying out the processes shown in FIG. 16A and FIG. 16B are plotted. From the template-matched patterns on each image frame, nanoparticles associated with binding (curve 782) and unbinding (curve 780) were determined, from which the net number of nanoparticles bound to the surface was counted (difference between curve 782 and curve 780).

Figure 17:
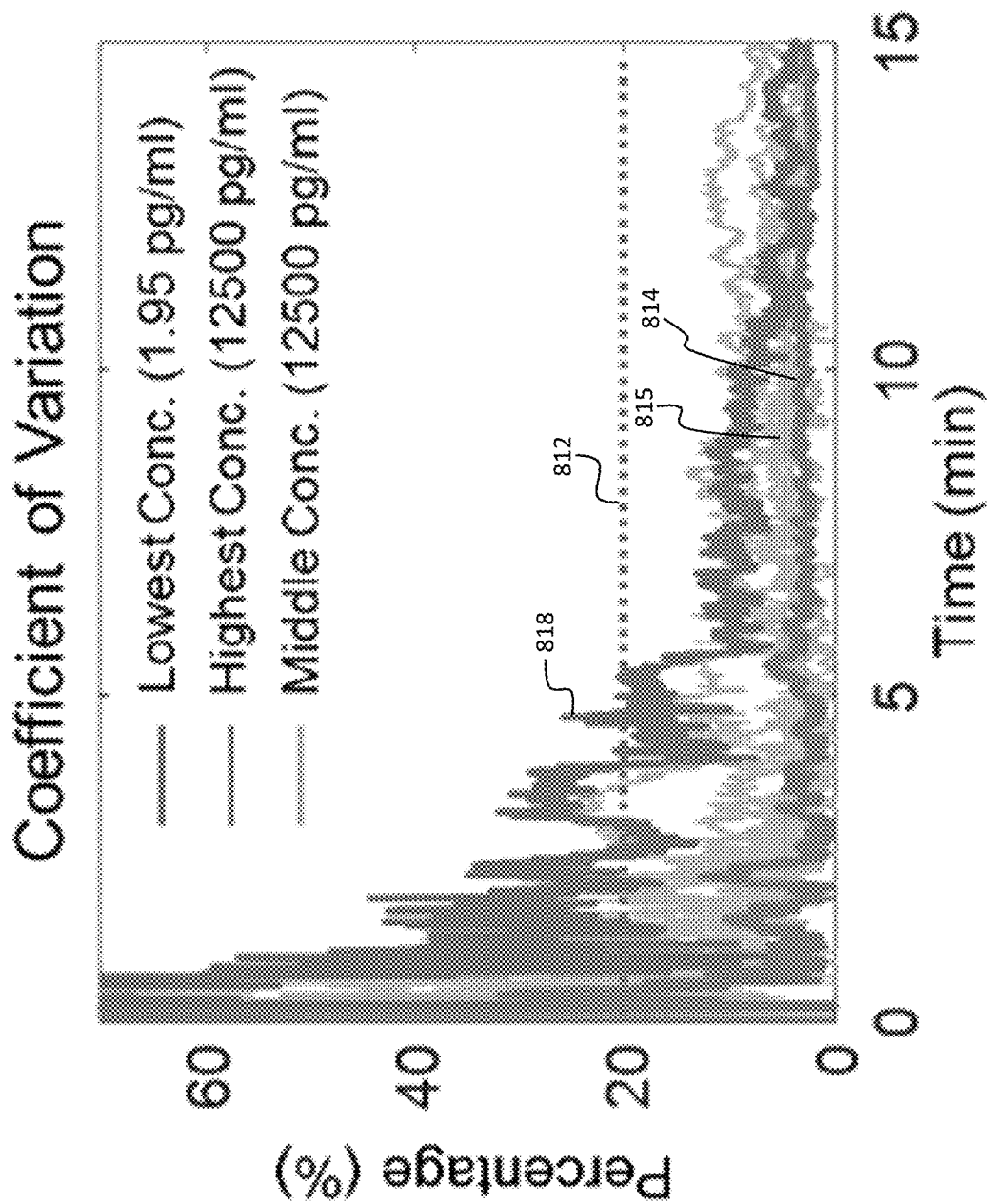
FIG. 17 shows time dependence of coefficient of variation for PCT time in the present TF-ELISA measurements

Referring now to FIG. 17, an evaluation of time dependence of coefficient of variation for PCT time in the present TF-ELISA measurements is presented. The dotted horizontal line 812 indicates 20% coefficient of variation. Plot 814 represents the coefficient of variation for the highest concentration of nanoparticles 12500 pg/ml. Plot 815 represents the coefficient of variation for the middle concentration of nanoparticles 12500 pg/ml. Plot 818 represents the coefficient of variation for the lowest concentration of nanoparticles, 1.95 pg/ml.

Figure 18:
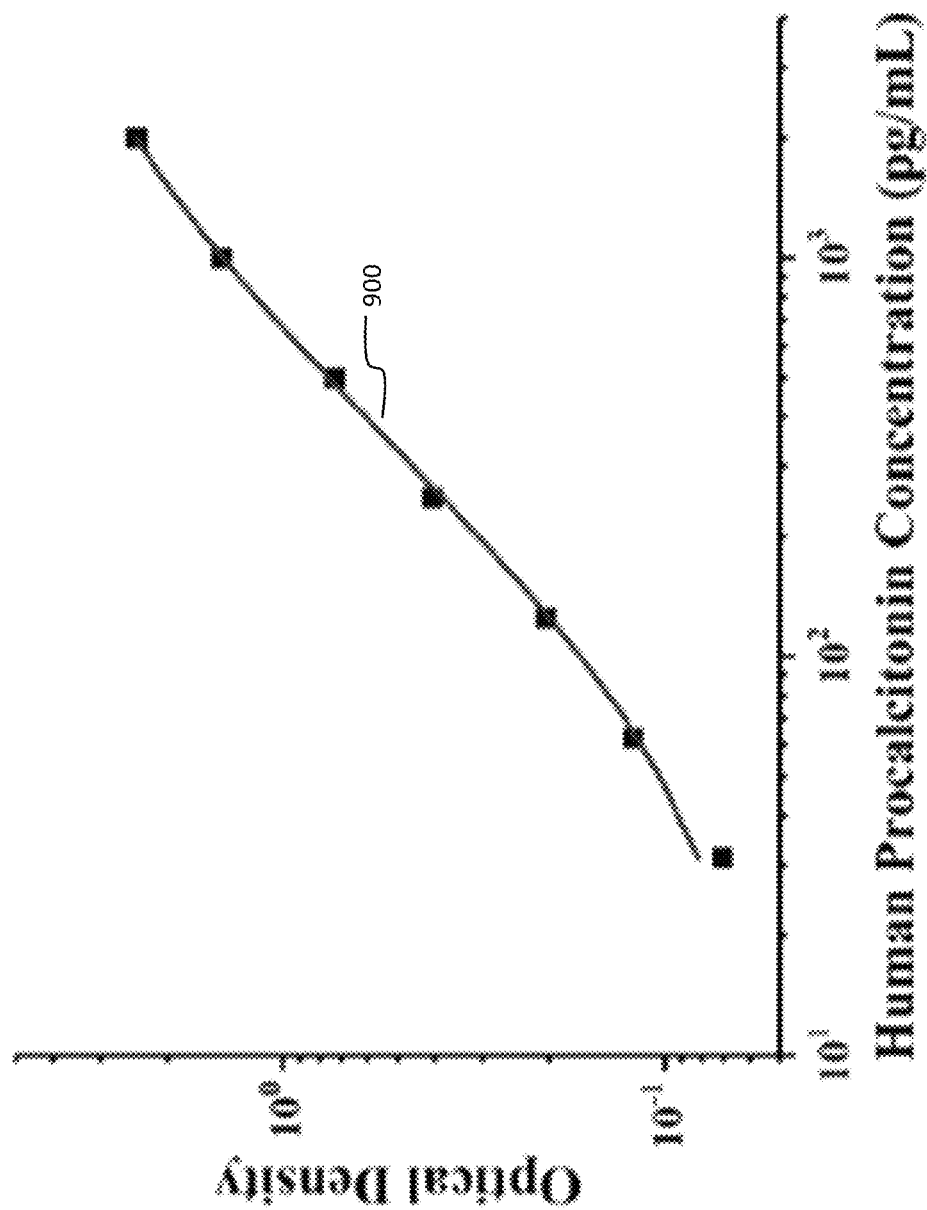
FIG. 18 shows a log-log plot of signal output showing a response of 2 logs, ranging from 31.3 pg/mL to 2000 pg/mL following the instructions of the ELISA kit.

Referring now to FIG. 18, a log-log plot of signal output (r-square=0.9992 showing a response of 2 logs, range from 31.3 pg/mL to 2000 pg/mL following the instructions of the ELISA kit is shown. Curve 900 is a plot of optical density versus human procalcitonin concentration in pg/ml. The standard curve 900 obtained by the conventional ELISA for PCT shows a logarithmic response with a dynamic range of 62.6 pg/mL to 2000 pg/mL and a limit of detection of 31.3 pg/mL. The standard curve from the present plasmonic imaging-based TD-ELISA has a broader dynamic range (5 logs vs. 2 logs), a lower limit of detection (2.76 pg/mL vs. 31.3 pg/mL) and a lower limit of quantitation (4 pg/mL vs. 62.6 pg/mL).

Referring now to FIG. 19, there shown is a table of values for TD-ELISA detection of IgG/anti-IgG binding. The standard curve of the IgG/anti-IgG binding can be fitted with an empirical equation widely used in ELISA, which is given by $$y = A_2 + \frac{A_1 - A_2}{1 + \left(\frac{X}{X_0}\right)p} \quad (1)$$

with r-square of 0.9986.

Comparison with Conventional ELISA Method Using PCT Spiked Serum Samples

Figures 20A, 20B, 20C:
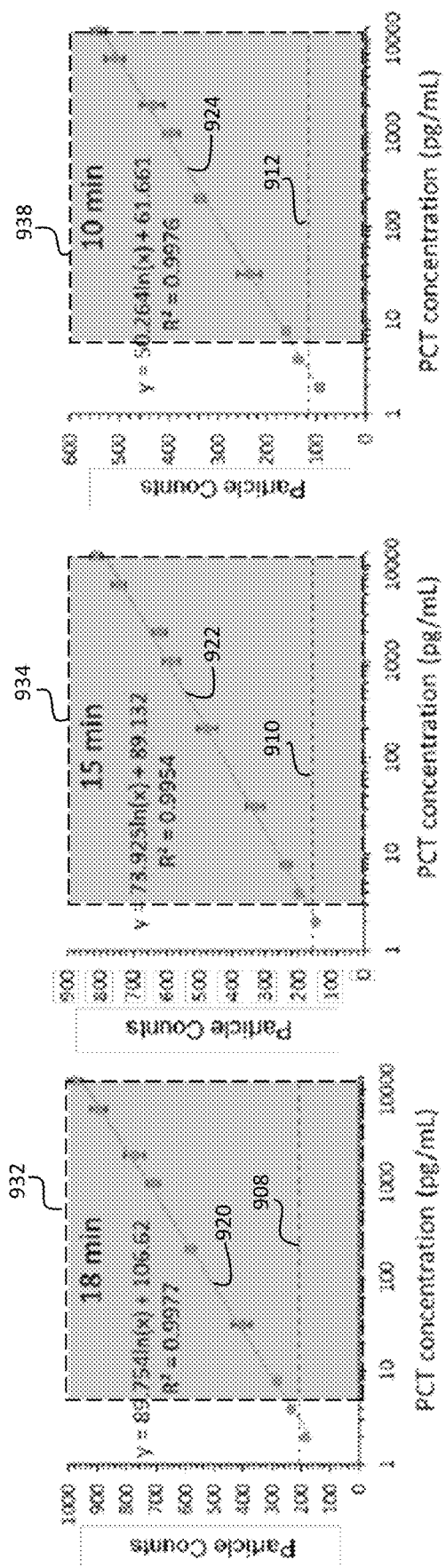

Referring now jointly to FIG. 20A-FIG. 20B, in order to investigate the correlation between the time-resolved digital immunoassay method with current conventional ELISA methods, PCT spiked serum samples with concentrations of 20, 200, and 2000 pg/mL were tested by both methods. The output values and recovery ratios are shown in Table 1. Time-resolved digital immunoassay results were analyzed by data from the first 5 minutes. The mean and standard deviation were calculated based on the PCT standard curve at 5 minutes (See FIG. 11D). The measurement was repeated three times. Recovery of each PCT spiked serum measurement concentration shows the accuracy of using established standard curves for serum sample analysis. The results show that the serum had no effect on the accuracy of the test. Both the disclosed methods and conventional ELISA methods can accurately predict the PCT concentrations of 200 and 2000 pg/mL. However, the conventional ELISA cannot predict 20 pg/mL due to a higher detection limit. Therefore, the disclosed method has a good application prospect in the serological detection of PCT.

TABLE 1

PCT spiked serum calculated respectively by the standard curve
of TD-ELISA counting and conventional ELISA.

| PCT Concentration (pg/mL) | TD-ELISA* (pg/mL) (This work) | Recovery (%) | Replicates | Conventional ELISA (pg/mL) | Recovery (%) | Replicates |
|---|---|---|---|---|---|---|
| 20 | 21.4 ± 0.4 | 107 ± 2.1 | 3 | NA | NA | 3 |
| 200 | 215.7 ± 30 | 95.5 ± 15 | 3 | 197.63 ± 7.8 | 98.5 ± 3.9 | 3 |
| 2000 | 2010 ± 284.8 | 100.5 ± 14.2 | 3 | 1923.24 ± 114.4 | 96.2 ± 5.7 | 3 |

*The results of TD-ELISA are the mean and standard deviation calculated based on the standard curve of time resolved digital immunoassay measurements of PCT at 5 min (supplementary information). Each measurement is replicated three times. Recovery (%) is the measured PCT concentration over the actual PCT concentration, which describes the accuracy of each technique.

Comparison of Different PCT Detection Technologies

Table 2 compares the performance of different PCT detection techniques in terms of sample volume, incubation, total detection time, limit of detection, limit of quantitation, and dynamic range. The TD-ELISA platform presented here can detect PCT in 100 µL of serum samples with a detection limit of 2.8 pg/mL and a limit of quantitation of 4 pg/mL for a total of 25 min, and dynamic range of ~5 logs. This performance is excellent compared to other sensitive PCT detection technologies listed in the table.

TABLE 2

Comparison of different PCT detection technologies

| | TD-ELISA (This work) | Convention al ELISA | ELECSYS BRAHMS PCT (Roche) | Quanterix SiMoA [39] | SMCxPRO™ (MilliporeSigma) [1] |
|---|---|---|---|---|---|
| Sample volume (µL) | 100 | 100 | 30 | 100 | 1.6 µL-3 µL |
| Incubation time | 10 min | 2 hour | 18 min | 20 min | 1 h |
| Total assay time | 25 min | 1-2 days | 3 h | >3 h | 1 day |
| LoD (pg/ml) | 2.8 | 30 | 20 | 0.44 | Not available |
| LoQ (pg/ml) | 4 | >30 | 60 | 1.23 | 0.05-2 |
| Dynamic range (pg/ml) | 4-12500 | 31.3-2000 | 20-10000 | 1.23-900 | >4 logs |

[1] The parameters of SMCxPRO™ was the theoretical value of the instrument, not specific obtained from PCT detection.

Referring now to FIG. 20A, a curve of PCT detection at time point 18 minutes is shown. The horizontal dashed line 908 shows the limit of detection, area 932 represents the dynamic range. Curve 920 is the fitted plot of article counts versus concentration. In each of the plots FIG. 20A-20F, because the PCT levels of sepsis patients are usually lower than 10000 pg/mL, PCT concentrations higher than 12500 pg/mL were not tested. The error bars in each plot are the standard deviation over triplicate test.

Referring now to FIG. 20B, a curve of PCT detection at time point 15 minutes is shown. The horizontal dashed line 910 shows the limit of detection, area 934 represents the dynamic range. Curve 922 is the fitted plot of article counts versus concentration.

Referring now to FIG. 20C, a curve of PCT detection at time point 10 minutes is shown. The horizontal dashed line 912 shows the limit of detection, area 938 represents the dynamic range. Curve 924 is the fitted plot of article counts versus concentration.

Referring now to FIG. 20D, a curve of PCT detection at time point 5 minutes is shown. The horizontal dashed line 926 shows the limit of detection, area 940 represents the dynamic range. Curve 944 is the fitted plot of article counts versus concentration.

Referring now to FIG. 20E, a curve of PCT detection at time point 4 minutes is shown. The horizontal dashed line 916 shows the limit of detection, area 942 represents the dynamic range. Curve 928 is the fitted plot of article counts versus concentration.

Referring now to FIG. 20F, a curve of PCT detection at time point 3 minutes is shown. The horizontal dashed line 918 shows the limit of detection, area 944 represents the dynamic range. Curve 930 is the fitted plot of article counts versus concentration.

As shown in the above description, the inventors have developed a time-resolved digital immunoassay by combining plasmonic imaging and automated counting of single gold nanoparticles. The high contrast plasmonic imaging allows accurate tracking of each nanoparticle. This capability, together with real-time imaging, leads to resolving multiple nanoparticle binding to an area smaller than the diffraction limit, leading to highly accurate detection of single binding events with a wide dynamic range. The inventors validated the principle with IgG binding to anti-IgG and demonstrated the performance of the immunoassay using PCT in controlled buffer and in sera with a limit of detection of 2.76 pg/mL, limit of quantification of 4 pg/mL, dynamic range of 0-$10^5$ pg/mL, and detection time of <25 mins for low concentration samples (a few pg/mL). the disclosed data also shows that the real-time counting can significantly shorten the detection time for high concentration samples (more relevant to sepsis patients). The inventors anticipate that this time-resolved digital immunoassay is particularly useful for diagnosing and tracking progression of acute diseases (e.g., sepsis and cardiovascular diseases), where rapid and precise biomarker quantification is needed.

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The contents of the following references are incorporated herein by this reference.

[1]. A. Mordente, E. Meucci, G. E. Martorana and A. Silvestrini, Adv. Exp. Med. Biol., 2015, 867, 9-26.[2] Diacom C C, Balaceami A, Moroşan E. Sepsis biomarkers. Past, present and future. Farmacia 2015; 63:811-815.

[3] C. Desmet, L. J. Blum, C. A. Marquette, Multiplex microarray ELISA versus classical ELISA, a comparison study of pollutant sensing for environmental analysis, Environ. Sci.: Process. Impacts 15 (2013) 1876-1882

[4] Rissin, D. M. et al. Single-molecule enzyme-linked immunosorbent assay detects serum proteins at subfemtomolar concentrations. Nature Biotechnol. 28, 595-599 (2010).

[5] Fischer, S. K.; Joyce, A.; Spengler, M.; Yang, T.-Y.; Zhuang, Y.; Fjording, M. S.; Mikulskis, A. AAPS J. 2015, 17, 93-101.

[6] Sevenler, D.; Daaboul, G. G.; Kanik, F. E.; Unlu, N. L.; Unlu, M. S., Digital Microarrays: Single-Molecule Readout with Interferometric Detection of Plasmonic Nanorod Labels. Acs Nano 2018, 12 (6), 5880-5887.

[7] Zhu, L.; Li, G. H.; Sun, S. Q.; Tan, H.; He, Y. H., Digital immunoassay of a prostate-specific antigen using gold nanorods and magnetic nanoparticles. Rsc Advances 2017, 7 (44), 27595-27602.

[8] Pei, X. J.; Yin, H. Y.; Lai, T. C.; Zhang, J. L.; Liu, F.; Xu, X.; Li, N., Multiplexed Detection of Attomoles of Nucleic Acids Using Fluorescent Nanoparticle Counting Platform. Analytical Chemistry 2018, 90 (2), 1376-1383.

[9] P. Jarolim, High sensitivity cardiac troponin assays in the clinical laboratories, Clin. Chem. Lab. Med. 53 (5) (2015) 635-652.

[10] Twerenbold R, Boeddinghaus J, Nestelberger T, Wildi K, Rubini Gimenez M, Badertscher P, Mueller C. Clinical use of high-sensitivity cardiac troponin in patients with suspected myocardial infarction. J Am Coll Cardiol. 2017; 70:996-1012. doi: 10.1016/j.jacc.2017.07.718

[11] Raphael Twerenbold, Allan Jaffe, Tobias Reichlin, Miriam Reiter, and Christian Mueller. High-sensitive troponin T measurements: what do we gain and what are the challenges? European Heart Journal (2012) 33, 579-586.

[12] Liang, K.; Liu, F.; Fan, J.; Sun, D. L.; Liu, C.; Lyon, C. J.; Bernard, D. W.; Li, Y.; Yokoi, K.; Katz, M. H.; Koay, E. J.; Zhao, Z.; Hu, Y., Nanoplasmonic quantification of tumour-derived extracellular vesicles in plasma microsamples for diagnosis and treatment monitoring. Nature Biomedical Engineering 2017, 1 (4).

[13] Diaconu, C. C.; Balaceanu, A.; Morosan, E., SEPSIS BIOMARKERS. PAST, PRESENT AND FUTURE. Farmacia 2015, 63 (6), 811-815.

[14] Mordente, A.; Meucci, E.; Martorana, G. E.; Silvestrini, A., Cancer Biomarkers Discovery and Validation: State of the Art, Problems and Future Perspectives. Advances in Cancer Biomarkers: from Biochemistry to Clinic for a Critical Revision 2015, 867, 9-26.

[15] Solier, C.; Langen, H., Antibody-based proteomics and biomarker research-Current status and limitations. Proteomics 2014, 14 (6), 774-783.

[16] Uludag, Y.; Tothill, I. E., Cancer Biomarker Detection in Serum Samples Using Surface Plasmon Resonance and Quartz Crystal Microbalance Sensors with Nanoparticle Signal Amplification. Analytical Chemistry 2012, 84 (14), 5898-5904.

[17] Satija, J.; Punjabi, N.; Mishra, D.; Mukherji, S., Plasmonic-ELISA: expanding horizons. Rsc Advances 2016, 6 (88), 85440-85456.

[18] Cheng, Z.; Choi, N.; Wang, R.; Lee, S.; Moon, K. C.; Yoon, S. Y.; Chen, L. X.; Choo, J., Simultaneous Detection of Dual Prostate Specific Antigens Using Surface-Enhanced Raman Scattering-Based Immunoassay for Accurate Diagnosis of Prostate Cancer. Acs Nano 2017, 11 (5), 4926-4933.

[19] Zhao, Y. F.; Cao, M. F.; McClelland, J. F.; Shao, Z. Y.; Lu, M., A photoacoustic immunoassay for biomarker detection. Biosensors & Bioelectronics 2016, 85, 261-266.

[20] Tighe, P. J.; Ryder, R. R.; Todd, I.; Fairclough, L. C., ELISA in the multiplex era: Potentials and pitfalls. Proteomics Clinical Applications 2015, 9 (3-4), 406-422.

[21] Gan, S. D.; Patel, K. R., Enzyme Immunoassay and Enzyme-Linked Immunosorbent Assay. Journal of Investigative Dermatology 2013, 133 (9), E10-E12.

[22] Desmet, C.; Blum, L. J.; Marquette, C. A., Multiplex microarray ELISA versus classical ELISA, a comparison study of pollutant sensing for environmental analysis. Environmental Science-Processes & Impacts 2013, 15 (10), 1876-1882.

[23] Rissin, D. M.; Kan, C. W.; Campbell, T. G.; Howes, S. C.; Fournier, D. R.; Song, L.; Piech, T.; Patel, P. P.; Chang, L.; Rivnak, A. J.; Ferrell, E. P.; Randall, J. D.; Provuncher, G. K.; Walt, D. R.; Duffy, D. C., Single-molecule enzyme-linked immunosorbent assay detects serum proteins at subfemtomolar concentrations. Nature Biotechnology 2010, 28 (6), 595-599.

[24] Chen, S.; Svedendahl, M.; Van Duyne, R. P.; Kall, M., Plasmon-Enhanced Colorimetric ELISA with Single Molecule Sensitivity. Nano Letters 2011, 11 (4), 1826-1830.

[25] Cohen, L.; Walt, D. R., Single-Molecule Arrays for Protein and Nucleic Acid Analysis. Annual Review of Analytical Chemistry, Vol 10 2017, 10, 345-363.

[26] Fischer, S. K.; Joyce, A.; Spengler, M.; Yang, T. Y.; Zhuang, Y.; Fjording, M. S.; Mikulskis, A., Emerging Technologies to Increase Ligand Binding Assay Sensitivity. Aaps Journal 2015, 17 (1), 93-101.

[27] Nam, J. M.; Thaxton, C. S.; Mirkin, C. A., Nanoparticle-based bio-bar codes for the ultrasensitive detection of proteins. Science 2003, 301 (5641), 1884-1886.

[28] Thaxton, C. S.; Elghanian, R.; Thomas, A. D.; Stoeva, S. I.; Lee, J. S.; Smith, N. D.; Schaeffer, A. J.; Klocker, H.; Horninger, W.; Bartsch, G.; Mirkin, C. A., Nanoparticle-based bio-barcode assay redefines "undetectable" PSA and biochemical recurrence after radical prostatectomy. Proceedings of the National Academy of Sciences of the U.S. Pat. No. 2,009,106 (44), 18437-18442.

[29] Liang, K.; Liu, F.; Fan, J.; Sun, D. L.; Liu, C.; Lyon, C. J.; Bernard, D. W.; Li, Y.; Yokoi, K.; Katz, M. H.; Koay, E. J.; Zhao, Z.; Hu, Y., Nanoplasmonic quantification of tumour-derived extracellular vesicles in plasma microsamples for diagnosis and treatment monitoring. Nature Biomedical Engineering 2017, 1 (4).

[30] Zhu, L.; Li, G. H.; Sun, S. Q.; Tan, H.; He, Y. H., Digital immunoassay of a prostate-specific antigen using gold nanorods and magnetic nanoparticles. Rsc Advances 2017, 7 (44), 27595-27602.

[31] Liao, T.; Yuan, F.; Yu, H. Y.; Li, Z., An ultrasensitive ELISA method for the detection of procalcitonin based on magnetic beads and enzyme-antibody labeled gold nanoparticles. Analytical Methods 2016, 8 (7), 1577-1585.

[32] Mordente, A.; Meucci, E.; Martorana, G. E.; Silvestrini, A., Cancer Biomarkers Discovery and Validation: State of the Art, Problems and Future Perspectives. Advances in Cancer Biomarkers: from Biochemistry to Clinic for a Critical Revision 2015, 867, 9-26.

[33] Rhodes, A.; Evans, L. E.; Alhazzani, W.; Levy, M. M.; Antonelli, M.; Ferrer, R.; Kumar, A.; Sevransky, J. E.; Sprung, C. L.; Nunnally, M. E.; Rochwerg, B.; Rubenfeld, G. D.; Angus, D. C.; Annane, D.; Beale, R. J.; Bellinghan, G. J.; Bernard, G. R.; Chiche, J. D.; Coopersmith, C.; De Backer, D. P.; French, C. J.; Fujishima, S.; Gerlach, H.; Hidalgo, J. L.; Hollenberg, S. M.; Jones, A. E.; Karnad, D. R.; Kleinpell, R. M.; Koh, Y.; Lisboa, T. C.; Machado, F. R.; Marini, J. J.; Marshall, J. C.; Mazuski, J. E.; McIntyre, L. A.; McLean, A. S.; Mehta, S.; Moreno, R. P.; Myburgh, J.; Navalesi, P.; Nishida, O.; Osborn, T. M.; Perner, A.; Plunkett, C. M.; Ranieri, M.; Schorr, C. A.; Seckel, M. A.; Seymour, C. W.; Shieh, L.; Shukri, K. A.; Simpson, S. Q.; Singer, M.; Thompson, B. T.; Townsend, S. R.; Van der Poll, T.; Vincent, J. L.; Wiersinga, W. J.; Zimmerman, J. L.; Dellinger, R. P., Surviving Sepsis Campaign: International Guidelines for Management of Sepsis and Septic Shock: 2016. Intensive Care Medicine 2017, 43 (3), 304-377.

[34] Liu, Y.; Hou, J. H.; Li, Q.; Chen, K. J.; Wang, S. N.; Wang, J. M., Biomarkers for diagnosis of sepsis in patients with systemic inflammatory response syndrome: a systematic review and meta-analysis. Springerplus 2016, 5.

[35] Wang, S. P.; Shan, X. N.; Patel, U.; Huang, X. P.; Lu, J.; Li, J. H.; Tao, N. J., Label-free imaging, detection, and mass measurement of single viruses by surface plasmon resonance. Proceedings of the National Academy of Sciences of the U.S. Pat. No. 2,010,107 (37), 16028-16032.

[36] Yu, H.; Shan, X. N.; Wang, S. P.; Chen, H. Y.; Tao, N. J., Molecular Scale Origin of Surface Plasmon Resonance Biosensors. Analytical Chemistry 2014, 86 (18), 8992-8997.

[37] Sriram, M.; Markhali, B. P.; Nicovich, P. R.; Bennett, D. T.; Reece, P. J.; Hibbert, D. B.; Tilley, R. D.; Gaus, K.; Vivekchand, S. R. C.; Gooding, J. J., A rapid readout for many single plasmonic nanoparticles using dark-field microscopy and digital color analysis. Biosensors & Bioelectronics 2018, 117, 530-536.

[38] Shrivastava, A.; Gupta, V B., Methods for the determination of limit of detection and limit of quantitation of the analytical methods. Chron Young Sci 2011, 2, 21-5.

[39] Carcamo Yañez, V A.; Göpfert, J C.; Otto.; M, Tumani H.; Peter, A.; Joos T., Development and Validation of an Ultrasensitive Procalcitonin Sandwich Immunoassay. High Throughput 2017, 6:18.

What is claimed is:

1. A system for quantitative detection of a biomarker in a fluid, comprising:
   a fluidic microchannel;
   a sensor surface on which a first antibody is attached that can bind specifically with the biomarker;
   a delivery device for introducing a fluidic sample containing the biomarker to the sensor surface along the microchannel and allowing the biomarker to be bound to the first antibody;
   an illumination source positioned to illuminate the sensor surface;
   an optical imaging system configured to capture light scattered by individual binding events of the biomarker to the first antibody on the sensor surface, and configured to generate sequential frames of images of at least a portion of the sensor surface including at least two zones;
   an image processing unit, coupled to receive data transmitted from the optical imaging system, being configured to quantify the individual binding events on the sensor surface at the at least two zones, being configured to determine a difference in numbers of binding events on multiple zones of the at least two zones, and being configured to evaluate relative statistical error in the difference in numbers of binding events obtained by comparison of different frames of images of the sequential frames of images to determine sufficiency of a detection time; and
   a data calibration system that correlates the difference in the number of binding events on any two zones to the concentration of the biomarker.

2. The system of claim 1, containing the fluidic sample introduced through the delivery device, wherein the fluidic sample is pre-mixed with nanoparticles coated with a second antibody, which conjugate with the biomarker and the first antibody on the sensor surface.

3. The system of claim 2, wherein the optical imaging system forms an image of the nanoparticles on the sensor surface, the image processing unit is configured to quantify the number of the nanoparticles on the sensor surface over the at least two zones in real time, and the image processing unit is configured to determine the difference in the numbers of the nanoparticles on a first zone and a second zone of the at least two zones, and the data calibration system is configured to correlate the difference in the numbers of nanoparticles on the first zone and the second zone to the concentration of the biomarker.

4. The system of claim 1, wherein the delivery device introduces nanoparticles coated with a second antibody to the fluidic microchannel, following introducing the fluidic sample containing the biomarker so as to conjugate with the biomarker captured by the first antibody on the sensor surface.

5. The system of claim 4, wherein the optical imaging system forms an image of the nanoparticles on the sensor surface;
   the image processing unit is configured to quantify the number of the nanoparticles on the sensor surface for the at least two zones in real time, and is configured to determine a difference in the numbers of the nanoparticles on a first zone and a second zone of the at least two zones; and
   the data calibration system is configured to correlate the difference in the number of nanoparticles on the first zone and the second zone to the concentration of the biomarker.

6. The system of claim 1, wherein the sensor surface is a surface plasmon resonance sensor surface, and the optical imaging system is based on surface plasmon resonance.

7. The system of claim 1 wherein the image processing unit is further configured to minimize background noise by subtracting initial frames of images of the sequential frames of images captured before the individual binding events obtained by comparison of subsequent frames of images of the sequential frames of images, and by performing averaging of multiple frames of the sequential frames of images.

8. The system of claim 1, wherein the number of zones is more than 2 and are treated as a continuous surface with varying number of binding events in the direction of the flow, rather than discrete zones.

9. The system of claim 1 wherein the image processing unit comprises a processor configured to perform the following functions:
- noise reduction filtering to reduce noise while maximizing signal to ensure that single nanoparticles can be imaged;
- imaging analysis to count individual nanoparticles in real time; and
- determining a difference in the counts of the numbers of binding events for the at least two zones along the fluidic microchannel, and comparing the difference in the numbers of binding events on a first zone and a second zone of the at least two zones to a concentration of the biomarker.

* * * * *